US009175282B2

(12) United States Patent
Watanabe et al.

(10) Patent No.: US 9,175,282 B2
(45) Date of Patent: Nov. 3, 2015

(54) CELLOBIOSE 2-EPIMERASE, ITS PREPARATION AND USES

(75) Inventors: Hikaru Watanabe, Okayama (JP);
Masahiro Yagi, Okayama (JP);
Tomoyuki Nishimoto, Okayama (JP);
Hiroto Chaen, Okayama (JP);
Shigeharu Fukuda, Okayama (JP)

(73) Assignee: HAYASHIBARA CO., LTD., OKAYAMA (JP)

( * ) Notice: Subject to any disclaimer, the term of this patent is extended or adjusted under 35 U.S.C. 154(b) by 36 days.

(21) Appl. No.: 13/590,460

(22) Filed: Aug. 21, 2012

(65) Prior Publication Data

US 2012/0329098 A1    Dec. 27, 2012

Related U.S. Application Data

(62) Division of application No. 13/147,965, filed as application No. PCT/JP2010/050928 on Jan. 25, 2010, now abandoned.

(30) Foreign Application Priority Data

Feb. 5, 2009    (JP) ................................ 2009-025070

(51) Int. Cl.
*C12P 19/02*      (2006.01)
*C12P 19/12*      (2006.01)
*C12N 9/90*       (2006.01)

(52) U.S. Cl.
CPC . *C12N 9/90* (2013.01); *C12P 19/02* (2013.01); *C12P 19/12* (2013.01)

(58) Field of Classification Search
None
See application file for complete search history.

(56) References Cited

U.S. PATENT DOCUMENTS

| 4,521,252 A | 6/1985 | Miyake et al. |
| 5,411,880 A | 5/1995 | Izumori et al. |
| 2010/0129865 A1 | 5/2010 | Maruta et al. |

FOREIGN PATENT DOCUMENTS

| GB | 2106912 A | 4/1983 |
| JP | 5823799 A | 2/1983 |
| JP | 58072598 A | 4/1983 |
| JP | 6125776 A | 5/1994 |
| JP | 10095794 A | 4/1998 |
| WO | 2007058086 A1 | 5/2007 |
| WO | 2008062555 A1 | 5/2008 |
| WO | 2009119538 A1 | 10/2009 |

OTHER PUBLICATIONS

Wilson et al., "Assessing Annotation Transfer for Genomics: Quantifying the Relations between Protein Sequence, Structure and Function through Traditional and Probabilistic Scores", J. Mol. Biol. 297:233-249, 2000.*
GenPept Accession No. Q2ZKZ6, "Putative N-acyl-D-glucosamine 2-epimerase", Nov. 2006, 1 page.*
"Oxford Dictionary of Biochemistry and Molecular Biology, Revised Edition", Oxford University Press, New York, 2006, pp. 334 and 617.*
Rainey et al., FEMS Micrbiol. Lett. 120:263-266, 1994.*
Masuda et al., Analytical Sci. 17:i895-i898, 2001.*
Itoh et al., J. Mol. Biol. 377:1443-1459, 2008.*
Supplementary European Search Report issued in corresponding European Application No. EP10738433 dated Sep. 12, 2012.
Park et al., Characterization of a recombinant cellobiose 2-epimerase from *Caldicellulosiruptor saccharolyticus* and its application in the production of mannose from glucose, Applied Microbiology and Biotechnology, 92(6):1187-1196 (2011).
Gherna, R. et al., "Catalogue of Bacteria and Phages", American Type Culture Collection, p. 470, 18th Edition, 1992.
Ito, Shigeaki et al., "Enzymatic properties of cellobiose 2-epimerase from *Ruminococcus albus* and the synthesis of rare oligosaccharides by the enzyme", Applied Microbiology and Biotechnology, vol. 79, pp. 433-441, 2008.
Ito, Shigeaki et al., "Cloning and sequencing of the cellobiose 2-epimerase gene from an obligatory anaerobe, *Ruminococcus albus*", Biochemical and Biophysical Research Communications, vol. 360, pp. 640-646, 2007.
NCBI, Accession YP_001179132, http://www.ncbi.nlm.nih.gov/protein/YP_001179132, 2007.
Nishimukai, Megumai et al., "Effects of Epilactose on Calcium Absorbotion and Serum Lipid Metabolism in Rats", Journal of Agricultural and Food Chemistry, vol. 56, pp. 10340-10345, 2008.
Pfeffer, Phillip E. et al., "Characterization of Keto Disaccharides in Solution by Deuterium-Induced, Differential Isotope-Shift C-N.M.R. Spectroscopy", Carbohydrate Research, vol. 102, pp. 11-22, 1982.
Taguchi Hidenori et al., "Cloning and sequencing of the gene for cellabiose 2-epimerase from a ruminal strain of *Eubacterium cellulosolvens*", FEMS Microbiology Letters, vol. 79, pp. 34-40, 2008.
Tyler, T.R. et al., "Epimerization of Dissacharides by Enzyme Preparations from *Ruminococcus albus*", Archives of Biochemistry and Biophysics, vol. 119, pp. 363-367, 1967.
Usui, Taichi et al., "C NMR Spectra of GLuco-mamno-oligosaccharides and Structurally Related Glucomannan", Agricultural Biological Chemistry, vol. 43, pp. 863-365, 1979.
Webb, Edwin C., "Enzyme Nomenclature", Academic Press Inc, USA, pp. 496-497, 1992.
Werken, Harmen J.G. van de et al., "Hydrogenomics of the Extremely Thermophilic Bacterium *Caldicellulosiruptor saccharolyticus*", Applied Environmental Microbiology, vol. 74, No. 21, pp. 6720-6729, 2008.
GenPept Accession No. ABP65941, Dec. 2008, 2 pages.
GenBank Accession No. CP000679 bases 318385 to 319287, Dec. 2008, 1 page.
Kim et al., Bioresource Technol. 104:668-672 (2012).
Park et al., Appl. Microbiol. Biotechnol., 92:1187-1196 (2011).

* cited by examiner

*Primary Examiner* — David J Steadman
(74) *Attorney, Agent, or Firm* — Browdy and Neimark, PLLC

(57) ABSTRACT

The present invention has objects to provide a thermostable cellobiose 2-epimerase, its preparation and uses. The present invention attains the above objects by providing a thermostable cellobiose 2-epimerase, a DNA encoding the enzyme, a recombinant DNA and transformant comprising the DNA, a process for producing the enzyme, and a process for producing isomerized saccharides using the enzyme.

2 Claims, 12 Drawing Sheets

SEQUENCE LISTING

<160> NUMBER OF SEQ ID NOS: 12

<210> SEQ ID NO 1
<211> LENGTH: 15
<212> TYPE: PRT
<213> ORGANISM: Caldicellulosiruptor saccharolyticus

<400> SEQUENCE: 1

Met Asp Ile Thr Arg Phe Lys Glu Asp Leu Lys Ala His Leu Glu
1               5                   10                  15

<210> SEQ ID NO 2
<211> LENGTH: 8
<212> TYPE: PRT
<213> ORGANISM: Caldicellulosiruptor saccharolyticus

<400> SEQUENCE: 2

Glu His Leu Val Asp Arg Arg Lys
1               5

<210> SEQ ID NO 3
<211> LENGTH: 7
<212> TYPE: PRT
<213> ORGANISM: Caldicellulosiruptor saccharolyticus

<400> SEQUENCE: 3

Gly Val Pro Val Asp Val Thr
1               5

<210> SEQ ID NO 4
<211> LENGTH: 7
<212> TYPE: PRT
<213> ORGANISM: Caldicellulosiruptor saccharolyticus

<400> SEQUENCE: 4

Tyr Leu Asp Ala Ala Ile Lys
1               5

<210> SEQ ID NO 5
<211> LENGTH: 17
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: n is a, c, g, or t

<400> SEQUENCE: 5
atggayatha cnagrtt                                              17

<210> SEQ ID NO 6
<211> LENGTH: 17
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 6

-continued

```
ttdatngcng crtcyaa                                                        17

<210> SEQ ID NO 7
<211> LENGTH: 24
<212> TYPE: DNA
<213> ORGANISM: Artificial sequence
<220> FEATURE:
<223> OTHER INFORMATION: synthetic

<400> SEQUENCE: 7
acaggagtaa aatctggtgg gttg                                                24

<210> SEQ ID NO 8
<211> LENGTH: 24
<212> TYPE: DNA
<213> ORGANISM: Artificial sequence
<220> FEATURE:
<223> OTHER INFORMATION: synthetic

<400> SEQUENCE: 8
ttcagcacat tgtaacatgc tgag                                                24

<210> SEQ ID NO 9
<211> LENGTH: 1170
<212> TYPE: DNA
<213> ORGANISM: Caldicellulosiruptor saccharolyticus

<400> SEQUENCE: 9 atg gat att aca agg ttt aag gaa gat tta aaa gct cat ctt gaa gaa           48
Met Asp Ile Thr Arg Phe Lys Glu Asp Leu Lys Ala His Leu Glu Glu
1               5                   10                  15 aag ata ata cca ttt tgg caa agt tta aag gac gat gaa ttt ggt ggc           96
Lys Ile Ile Pro Phe Trp Gln Ser Leu Lys Asp Asp Glu Phe Gly Gly
            20                  25                  30 tac tat gga tat atg gac ttt aat ctt aac att gac aga aaa gct caa          144
Tyr Tyr Gly Tyr Met Asp Phe Asn Leu Asn Ile Asp Arg Lys Ala Gln
        35                  40                  45 aaa ggt tgc att ttg aac tcg agg ata ttg tgg ttt ttc tca gca tgt          192
Lys Gly Cys Ile Leu Asn Ser Arg Ile Leu Trp Phe Phe Ser Ala Cys
    50                  55                  60 tac aat gtg ctg aaa agt gaa aaa tgc aaa gag atg gct ttt cat gcg          240
Tyr Asn Val Leu Lys Ser Glu Lys Cys Lys Glu Met Ala Phe His Ala
65                  70                  75                  80 ttt gaa ttt tta aaa aac aag ttt tgg gac aaa gag tat gaa gga ctt          288
Phe Glu Phe Leu Lys Asn Lys Phe Trp Asp Lys Glu Tyr Glu Gly Leu
                85                  90                  95 ttc tgg agt gta tcc cac aaa ggt gtg ccc gtt gat gtg aca aaa cat          336
Phe Trp Ser Val Ser His Lys Gly Val Pro Val Asp Val Thr Lys His
            100                 105                 110 gtt tat gtt cag gct ttt ggc ata tac ggg ctt tct gag tac tat gaa          384
Val Tyr Val Gln Ala Phe Gly Ile Tyr Gly Leu Ser Glu Tyr Tyr Glu
        115                 120                 125 gca tcc ggg gac gaa gaa gct ctt cat atg gct aag agg ctt ttc gag          432
Ala Ser Gly Asp Glu Glu Ala Leu His Met Ala Lys Arg Leu Phe Glu
    130                 135                 140 att tta gag aca aaa tgc aaa agg gaa aat gga tac aca gaa cag ttt          480
Ile Leu Glu Thr Lys Cys Lys Arg Glu Asn Gly Tyr Thr Glu Gln Phe
145                 150                 155                 160 gag aga aac tgg caa gaa aaa gaa aac agg ttt ttg agc gaa aat gga          528
Glu Arg Asn Trp Gln Glu Lys Glu Asn Arg Phe Leu Ser Glu Asn Gly
                165                 170                 175
```

| | | | | | | | | | | | | | | | | |
|---|---|---|---|---|---|---|---|---|---|---|---|---|---|---|---|---|
| gta | att | gcc | tca | aaa | aca | atg | aac | acg | cat | ctt | cat | gta | ctg | gag | agc | 576 |
| Val | Ile | Ala | Ser | Lys | Thr | Met | Asn | Thr | His | Leu | His | Val | Leu | Glu | Ser | |
| | | | 180 | | | | | 185 | | | | | 190 | | | |

```
gta att gcc tca aaa aca atg aac acg cat ctt cat gta ctg gag agc      576
Val Ile Ala Ser Lys Thr Met Asn Thr His Leu His Val Leu Glu Ser
            180             185             190 tac aca aac ctc tac agg ctt ttg aag ctt gat gat gtg tat gaa gcg      624
Tyr Thr Asn Leu Tyr Arg Leu Leu Lys Leu Asp Asp Val Tyr Glu Ala
            195             200             205 ctt gag tgg att gta aga ctc ttt gtt gac aag att tac aaa aaa gga      672
Leu Glu Trp Ile Val Arg Leu Phe Val Asp Lys Ile Tyr Lys Lys Gly
210             215             220 aca ggt cac ttc aag gta ttt tgc gat gat aac tgg aac gaa ctt ata      720
Thr Gly His Phe Lys Val Phe Cys Asp Asp Asn Trp Asn Glu Leu Ile
225             230             235             240 aaa gca gta tca tat gga cat gac att gaa gca agc tgg ctt tta gac      768
Lys Ala Val Ser Tyr Gly His Asp Ile Glu Ala Ser Trp Leu Leu Asp
            245             250             255 caa gct gcc aag tat ctg aag gat gaa aag tta aaa gag gag gtt gaa      816
Gln Ala Ala Lys Tyr Leu Lys Asp Glu Lys Leu Lys Glu Glu Val Glu
            260             265             270 aag ctc gca tta gag gtt gcc cag ata act tta aaa gaa gcc ttt gat      864
Lys Leu Ala Leu Glu Val Ala Gln Ile Thr Leu Lys Glu Ala Phe Asp
            275             280             285 ggt caa agt ctt ata aat gaa atg ata gaa gat agg att gac agg agt      912
Gly Gln Ser Leu Ile Asn Glu Met Ile Glu Asp Arg Ile Asp Arg Ser
290             295             300 aaa atc tgg tgg gtt gaa gca gag acg gtt gtt gga ttt ttc aat gca      960
Lys Ile Trp Trp Val Glu Ala Glu Thr Val Val Gly Phe Phe Asn Ala
305             310             315             320 tat caa aag aca aaa gag gaa aaa tat tta gat gca gcc atc aag aca     1008
Tyr Gln Lys Thr Lys Glu Glu Lys Tyr Leu Asp Ala Ala Ile Lys Thr
            325             330             335 tgg gag ttc ata aaa gag cat ctt gtt gac aga aga aag aac tct gaa     1056
Trp Glu Phe Ile Lys Glu His Leu Val Asp Arg Arg Lys Asn Ser Glu
            340             345             350 tgg ctg tgg aag gta aat gag gat tta gaa gct gta aat atg cca att     1104
Trp Leu Trp Lys Val Asn Glu Asp Leu Glu Ala Val Asn Met Pro Ile
            355             360             365 gtt gag caa tgg aag tgc cca tat cac aat ggc aga atg tgt ttg gag     1152
Val Glu Gln Trp Lys Cys Pro Tyr His Asn Gly Arg Met Cys Leu Glu
370             375             380 ata ata aaa agg gtt gac                                             1170
Ile Ile Lys Arg Val Asp
385             390
```

<210> SEQ ID NO 10
<211> LENGTH: 390
<212> TYPE: PRT
<213> ORGANISM: Caldicellulosiruptor saccharolyticus

<400> SEQUENCE: 10

```
Met Asp Ile Thr Arg Phe Lys Glu Asp Leu Lys Ala His Leu Glu Glu
1               5                   10                  15

Lys Ile Ile Pro Phe Trp Gln Ser Leu Lys Asp Asp Glu Phe Gly Gly
            20                  25                  30

Tyr Tyr Gly Tyr Met Asp Phe Asn Leu Asn Ile Asp Arg Lys Ala Gln
        35                  40                  45

Lys Gly Cys Ile Leu Asn Ser Arg Ile Leu Trp Phe Phe Ser Ala Cys
    50                  55                  60

Tyr Asn Val Leu Lys Ser Glu Lys Cys Lys Glu Met Ala Phe His Ala
65                  70                  75                  80
```

Phe Glu Phe Leu Lys Asn Lys Phe Trp Asp Lys Glu Tyr Glu Gly Leu
                 85                  90                  95

Phe Trp Ser Val Ser His Lys Gly Val Pro Val Asp Val Thr Lys His
            100                 105                 110

Val Tyr Val Gln Ala Phe Gly Ile Tyr Gly Leu Ser Glu Tyr Tyr Glu
        115                 120                 125

Ala Ser Gly Asp Glu Glu Ala Leu His Met Ala Lys Arg Leu Phe Glu
    130                 135                 140

Ile Leu Glu Thr Lys Cys Lys Arg Glu Asn Gly Tyr Thr Glu Gln Phe
145                 150                 155                 160

Glu Arg Asn Trp Gln Glu Lys Glu Asn Arg Phe Leu Ser Glu Asn Gly
                165                 170                 175

Val Ile Ala Ser Lys Thr Met Asn Thr His Leu His Val Leu Glu Ser
            180                 185                 190

Tyr Thr Asn Leu Tyr Arg Leu Leu Lys Leu Asp Asp Val Tyr Glu Ala
        195                 200                 205

Leu Glu Trp Ile Val Arg Leu Phe Val Asp Lys Ile Tyr Lys Lys Gly
    210                 215                 220

Thr Gly His Phe Lys Val Phe Cys Asp Asp Asn Trp Asn Glu Leu Ile
225                 230                 235                 240

Lys Ala Val Ser Tyr Gly His Asp Ile Glu Ala Ser Trp Leu Leu Asp
                245                 250                 255

Gln Ala Ala Lys Tyr Leu Lys Asp Glu Lys Leu Lys Glu Glu Val Glu
            260                 265                 270

Lys Leu Ala Leu Glu Val Ala Gln Ile Thr Leu Lys Glu Ala Phe Asp
        275                 280                 285

Gly Gln Ser Leu Ile Asn Glu Met Ile Glu Asp Arg Ile Asp Arg Ser
    290                 295                 300

Lys Ile Trp Trp Val Glu Ala Glu Thr Val Val Gly Phe Phe Asn Ala
305                 310                 315                 320

Tyr Gln Lys Thr Lys Glu Glu Lys Tyr Leu Asp Ala Ala Ile Lys Thr
                325                 330                 335

Trp Glu Phe Ile Lys Glu His Leu Val Asp Arg Arg Lys Asn Ser Glu
            340                 345                 350

Trp Leu Trp Lys Val Asn Glu Asp Leu Glu Ala Val Asn Met Pro Ile
        355                 360                 365

Val Glu Gln Trp Lys Cys Pro Tyr His Asn Gly Arg Met Cys Leu Glu
    370                 375                 380

Ile Ile Lys Arg Val Asp
385                 390

<210> SEQ ID NO 11
<211> LENGTH: 35
<212> TYPE: DNA
<213> ORGANISM: Artificial sequence
<220> FEATURE:
<223> OTHER INFORMATION: synthetic

<400> SEQUENCE: 11
cacacacacc atggatatta caaggtttaa ggaag                        35

<210> SEQ ID NO 12
<211> LENGTH: 38
<212> TYPE: DNA
<213> ORGANISM: Artificial sequence
<220> FEATURE:
<223> OTHER INFORMATION: synthetic

```
<400> SEQUENCE: 12
cacacacagg atccttagtc aaccttttt attatctc                                        38
```

CELLOBIOSE 2-EPIMERASE, ITS PREPARATION AND USES

FIELD OF THE INVENTION

The present invention relates to a cellobiose 2-epimerase, its preparation and uses, in particular, a cellobiose 2-epimerase which catalyzes aldose-ketose conversion as well as 2-epimerization, a process of producing thereof, a DNA encoding the enzyme, a recombinant DNA and a transformant thereof, and a process for producing isomerized saccharides using the enzyme.

BACKGROUND OF THE INVENTION

"Isomerase" is a generic term meaning a enzyme catalyzing conversion of isomers. According to "Enzyme Nomenclature", Academic Press Inc., USA, 1992, it includes the following six groups: (1) EC 5.1; racemases and epimerases catalyzing optical isomerization, (2) EC 5.2; enzymes catalyzing geometric conversion of cis-trans isomers, (3) EC 5.3; enzymes catalyzing aldose-ketose conversion, keto-enol tautomerization, and intramolecular rearrangement of double bond, (4) EC 5.4; enzymes catalyzing intramolecular rearrangement of substituent to produce structural isomers, (5) EC 5.5; enzymes catalyzing intramolecular lyase-reaction, and (6) EC 5.99; enzymes catalyzing other isomerization. Among these isomerases, for example, the following enzymes are well known as isomerases catalyzing isomerization of neutral saccharides: xylose isomerase (EC 5.3.1.5) catalyzing conversion between D-xylose and D-xylulose, or between D-glucose and D-fructose (aldose-ketose conversion), aldose 1-epimerase (EC 5.1.3.3) catalyzing conversion between α and β anomer of aldose, ketose 3-epimerase catalyzing epimerization of C-3 position of ketopentoses and ketohexoses to produce the corresponding epimers (q.v. Japanese Patent Kokai No. 125776/1994 or International Patent Publication No. WO 2007/058086). These enzymes are widely used for industrial production of isomerized saccharides, quantitative determination of saccharides, and preparation of rare saccharides.

On the other hand, Tyler et al., *Archives of Biochemistry and Biophysics*, Vol. 119, pp. 363-367 (1967), reported that *Ruminococcus albus*, an anaerobic bacteria, produces a cellobiose 2-epimerase, and it epimerizes C-2 position of reducing-terminal glucose in cellobiose to produce epicellobiose (4-O-β-D-Glucosyl D-mannose), which enzyme has been assigned a enzyme number of EC 5.1.3.11 in Enzyme Nomenclature referred to above. Ito et al., *Biochemical and Biophysical Research Communication*, Vol. 360, pp. 640-645 (2007) and Ito et al., *Applied Microbiology and Biotechnology*, Vol. 79, pp. 433-441 (2008) disclosed the amino-acid sequence of the cellobiose 2-epimerase, the DNA sequence encoding the amino-acid sequence, and that the cellobiose 2-epimerase acts on cellooligosaccharide or lactose, as well as cellobiose, to produce epicellooligosaccharide or epilactose (4-O-β-D-calactosyl D-mannnose). Furthermore, Taguchi et al., *FEMS Microbiology Letters*, Vol. 287, pp. 34-40 (2008), disclosed cellobiose 2-epimerase produced by *Eubacterium cellulosolvens*, also an anaerobic bacteria.

Nishimukai et al., *Journal of Agricultural and Food Chemistry*, Vol. 56, pp. 10340-10345 (2008) disclosed that when epilactose, converted from lactose by cellobiose 2-epimerase, was ingested in rat, it exerted physiological functions of promoting calcium absorption in the small intestine, increasing the amount of short-chain fatty acid in the intestine, and lowering the plasma cholesterol level, suggesting that epilactose is expected to be developed for a prebiotic material.

However, the above known cellobiose 2-epimerase have problems that they are hard to use for industrial production of epilactose or epicellobiose because of their low heat-resistance. Heat-resistance is an important property for practical application of enzyme reaction, and a highly heat-resistant enzyme is economically beneficial because a longtime reaction can be carried out with a small amount of the enzyme, resulting in low consumption of the enzyme. In consideration of industrial use, enzyme reaction is preferable to be conducted at 55° C. or more, preferably, 60° C. or more. In the above regard, a cellobiose 2-epimerase with higher heat-resistance is desired.

DISCLOSURE OF THE INVENTION

An object of the present invention is to provide a highly thermostable cellobiose 2-epimerase, its preparation and uses.

Under the circumstances mentioned above, to attain the object, the inventors of the present invention screened many thermophilic microorganisms to obtain a thermostable cellobiose 2-epimerase. As the result, the inventors found that a liquid disrupted-cell extract of *Caldicellusiruptor saccharolyticus* ATCC43494 in the genus of *Caldicellusiruptor*, had an enzyme activity of epimerizing lactose to form epilactose and producing a presumable isomerized saccharide from cellobiose. The inventors purified the epimerase as an electrophoretically single protein, investigated its properties, and found that the enzyme had thermostability up to 70° C. However, the yield of the purified enzyme is too small to investigate its substrate specificity in detail.

According to the amino-acid sequence of the epimerase, the inventors cloned the DNA encoding the epimerase from the genomic DNA of *Caldicellusiruptor saccharolyticus*, transformed *E. coli* with the recombinant DNA, and the transformant was cultured to prepare the recombinant enzyme. The inventors investigated the substrate specificity of the recombinant enzyme and found that the enzyme has wide substrate specificity, such as unexpectedly act on D-glucose or D-fructose among monosaccharides, maltose among disaccharides, and maltooliosaccharides and cellooligosaccharides with glucose polymerization degree of 3 or more among oligosaccharides, to produce the corresponding epimers, i.e., D-mannose, D-talose, epimaltose (4-O-α-D-glucosyl D-mannose) and epimaltooligosaccharides or epicellooligosaccharides with glucose polymerization degree of 3 or more, respectively, as well as epimerising cellobiose and lactose to form epicellobiose and epilactose, respectively.

The inventors also found that in addition to 2-epimerization, the enzyme also catalyzes aldose-ketose conversion in higher enzyme dosage, to convert D-glucose or D-mannose into D-fructose, D-galactose or D-talose into D-tagatose, maltose or epimaltose into maltulose (4-O-α-D-glucosyl D-fructose), cellobiose or epicellobiose into cellobiulose (4-O-β-D-glucosyl D-fructose), and lactose or epilactose into lactulose (4-O-β-D-galactosyl D-fructose). It was revealed that the enzyme is a novel cellobiose 2-epimerase catalyzing both 2-epimerization and aldose-ketose conversion.

On the basis of the above finding, the inventors established a process for producing the novel cellobiose 2-epimerase, a DNA encoding the enzyme, a recombinant DNA and a transformant thereof and a process for producing isomerised saccharide using the enzyme, and accomplished the present invention.

The present invention attains the above object by providing thermostable cellobiose 2-epimerase, a DNA encoding the enzyme, a recombinant DNA and a transformant thereof, and a process for producing isomerised saccharide using the enzyme.

The cellobiose 2-epimerase of the present invention is thermostable, and is able to be expressed largely with recombinant microorganism, and the recombinant enzyme is easy to be purified.

Using the cellobiose 2-epimerase of the present invention, D-mannose, epimaltose, episellobiose or cellobiulose, and epilactose or lactulose can be produced from D-glucose, maltose, cellobiose, and lactose, respectively, i.e., rare and high-valued saccharides can be produced from low-cost material saccharides in industrial scale.

EXPLANATIONS OF SYMBOLS

Figure 1:
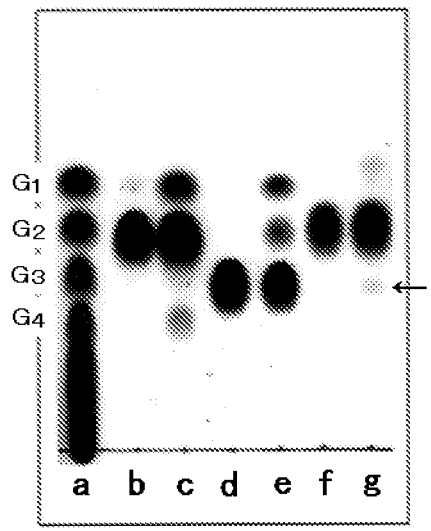
FIG. 1 shows a TLC chromatogram of the reaction mixture obtained by allowing a supernatant of the disrupted-cell extract of *Caldicellusiruptor saccharolyticus* ATCC43494 to act on cellobiose, lactose or epilactose.
Figure 2:
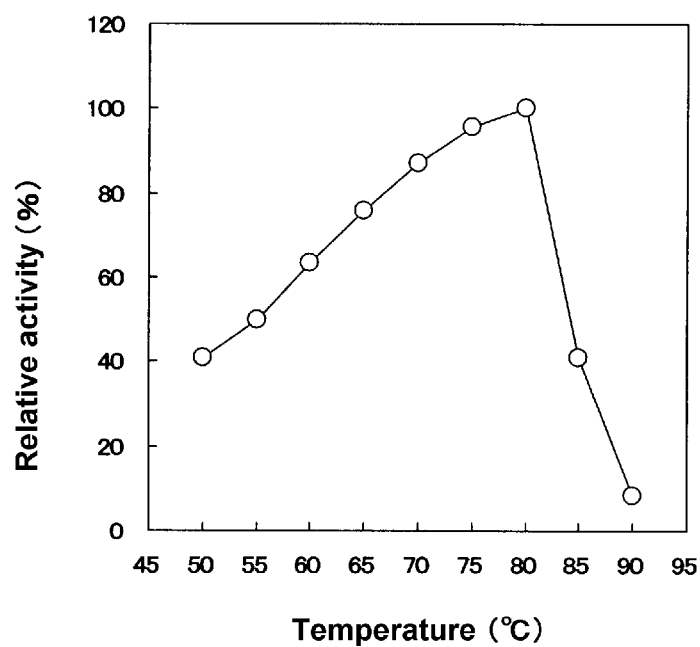
FIG. 2 shows the effect of temperature on the cellobiose 2-epimerase activity of the present invention.
Figure 6:
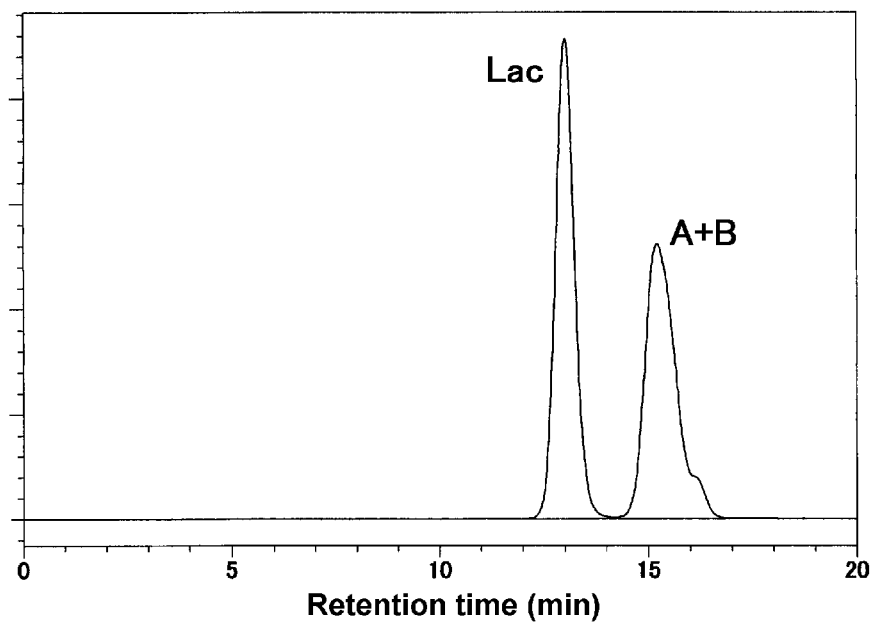
FIG. 6 shows a HPLC chromatogram of the reaction mixture obtained by allowing the cellobiose 2-epimerase of the present invention to act on lactose.
Figure 14:
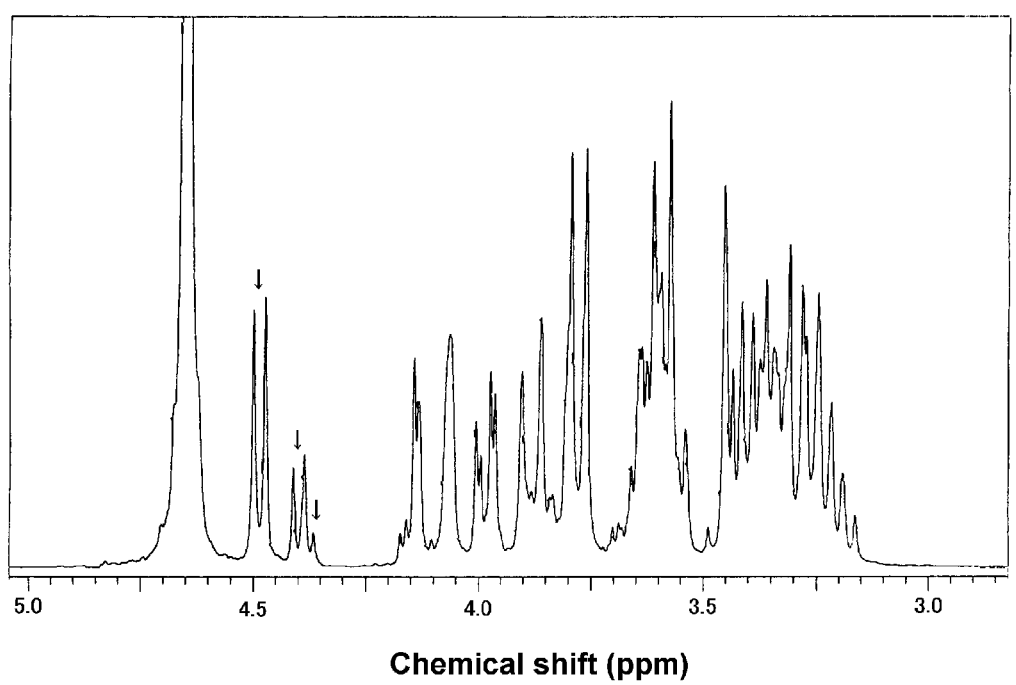
FIG. 14 shows a $^1$H-NMR spectrum of Isomerized Saccharide D isolated from the reaction mixture obtained by allowing the cellobiose 2-epimerase of the present invention to act on cellobiose.
Figure 15:
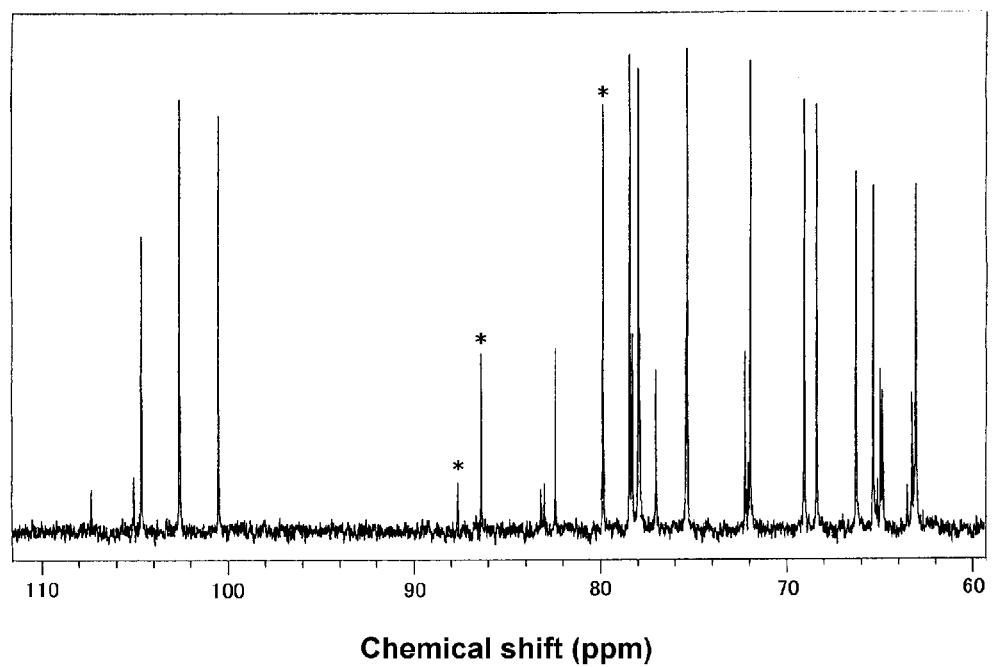
FIG. 15 shows a $^{13}$C-NMR spectrum of Isomerized Saccharide D isolated from the reaction mixture obtained by allowing the cellobiose 2-epimerase of the present invention to act on cellobiose.
Figure 17:
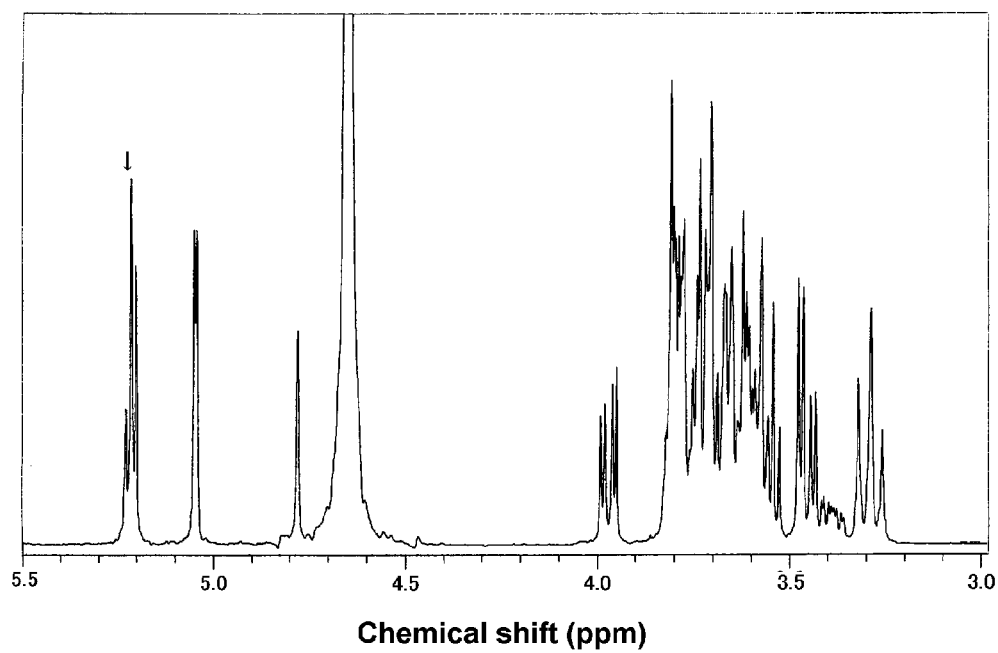
FIG. 17 shows a $^1$H-NMR spectrum of Isomerized Saccharide E isolated from the reaction mixture obtained by allowing the cellobiose 2-epimerase of the present invention to act on maltose.
Figure 18:
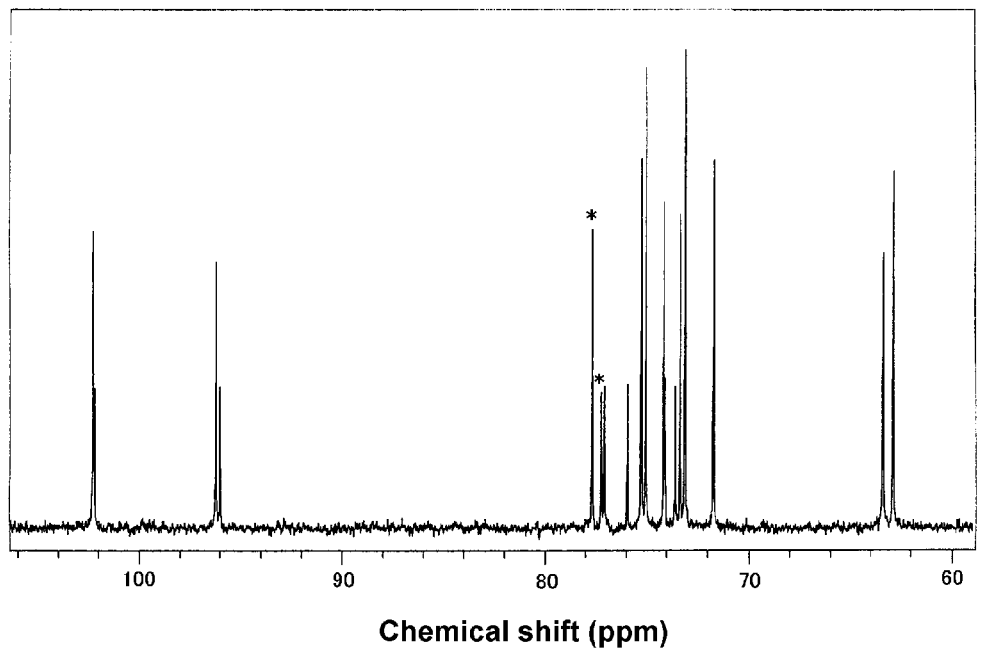
FIG. 18 shows a $^{13}$C-NMR spectrum of Isomerized Saccharide E isolated from the reaction mixture obtained by allowing the cellobiose 2-epimerase of the present invention to act on maltose.
Figure 22:
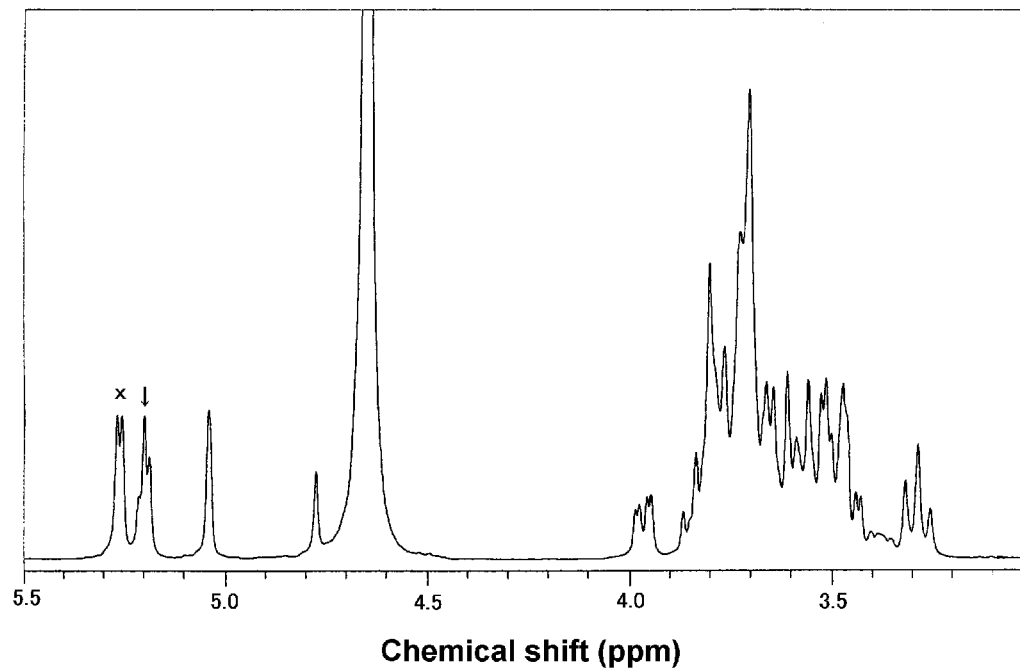
FIG. 22 shows a $^1$H-NMR spectrum of Isomerized Saccharide G isolated from the reaction mixture obtained by allowing the cellobiose 2-epimerase of the present invention to act on maltotriose.
Figure 23:
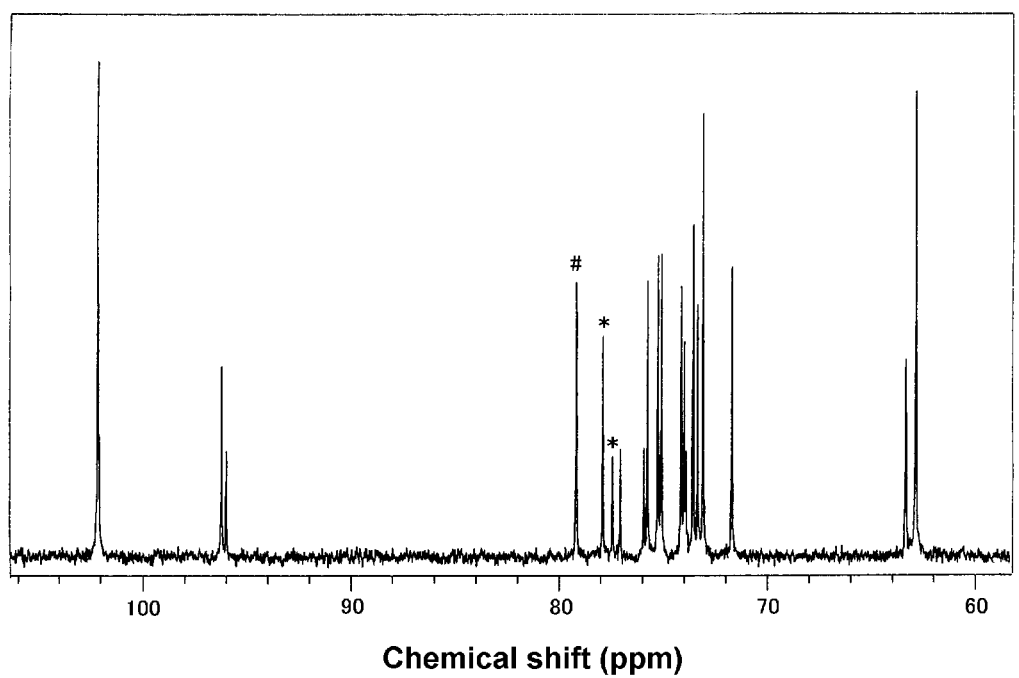
FIG. 23 shows a $^{13}$C-NMR spectrum of Isomerized Saccharide G isolated from the reaction mixture obtained by allowing the cellobiose 2-epimerase of the present invention to act on maltotriose.

In FIG. 1;
a: Mixture of maltooligosaccharides (as marker of glucose polymerization degree)
b: Cellobiose as a standard
C: Reaction mixture of cellobiose
d: Lactose as a standard
e: Reaction mixture of alactose
f: Epilactose as a standard
g: Reaction mixture of epilactose
←: Lactose (isomerized saccharide)
$G_1$: Glucose
$G_2$: Maltose
$G_3$: Maltotriose
$G_4$: Maltotetraose.
In FIG. 6;
Lac: Lactose
A+B: Mixture of Isomerized saccharides A and B
In FIG. 11;
Cel: Cellobiose
C: Isomerized saccharide C
D: Isomerized saccharide D
In FIGS. 12, 14 and 17;
↓: Signal of proton in C-1 position of D-glucose
In FIGS. 13, 18 and 23;
*: Signal of C-4 of D-mannose
In FIG. 15;
*: Signal of C-4 of D-fructose
In FIG. 16;
Mal: Maltose
E: Isomerized saccharide E
F: Isomerized saccharide F
In FIG. 21;
$G_3$: Maltotriose
G: Isomerized saccharide G In FIG. 22;
↓: Signal of proton in C-1 position of D-glucose binding to D-mannose
x: Signal of proton in C-1 position of D-glucose binding to D-glucose
In FIG. 23;
: Signal of C-4 of D-glucose bound by D-glucose

BEST MODE FOR CARRYING OUT THE INVENTION

The cellobiose 2-epimerase of the present invention is an enzyme catalyzing isomerization, more concretely, 2-epimerization and aldose-ketose conversion as follows:

(1) 2-Epimerization epimerizing C-2 position of D-glucose or D-galactose to convert them into D-mannnose or talose, respectively, and also catalyzing their reverse reactions;

epimerising C-2 position of the reducing end glucose of maltose, cellobiose or lactose to convert them into epimaltose, epicellobiose or epilactose, respectively; and epimerizing C-2 position of the reducing end glucose of maltooligosaccharides and celloligosaccharides to convert them into epimaltooligosaccharides and epicelloligosaccharides, respectively.

(2) Aldose-Ketose Conversion converting D-glucose or D-mannnose into D-fructose, D-galactose or D-talose into D-tagatose, and also catalyzing their reverse reactions;

converting maltose or epimaltose into maltulose, cellobiose or epicellobiose into cellobiulose, and lactose or epilactose into lactulose.

The cellobiose 2-epimerase of the present invention has the following physicochemical properties, as a concrete example:

(1) Molecular Weight
44,000±5,000 daltons on SDS-gel electrophoresis;
(2) Optimum Temperature
80° C. when reacted at pH 6.0 for 20 minutes;
(3) Optimum pH
pH 7.8 when reacted at 50° C. for 20 minutes;
(4) Thermostability
Stable up to 70° C. when incubated at pH 6.0 for 60 minutes;
(5) pH stability
Stable in a range of pH 4.5 to 9.5 when incubated at 4° C. for 24 hours.

Through the specification of the present invention, the activity of the cellobiose 2-epimerase was determined as a lactose 2-epimerase activity, which catalyzes epimerization of lactose to form epilactose, using lactose as the substrate obtainable in highly purified form at low cost. The lactose 2-epimerase activity was measured as follows. To 1,000 µl of substrate solution, which contains lactose to give a final concentration of 35.1 mM and acetate buffer (pH 6.0) to give a final concentration of 20 mM of the reaction solution, 200 µl of a enzyme solution was added to give a 1,200 µl of the reaction solution, followed by reaction at 50° C. for 20 minutes. The reaction was stopped by heating for 10 minutes in a boiling water bath. Then reaction mixture was subjected to HPLC chromatography to determine the amount of epilactose produced by the reaction. The HPLC chromatography was conducted at the following conditions;

Column: "MCI Gel CK80EP" (produced by Mitsubishi Chemical Corporation, Tokyo, Japan)
Column temperature: 75° C.
Flow rate: 0.6 ml/min
Eluent: water
Detector: "RID-10A" (produced by Shimadzu Corporation, Kyoto, Japan).

One unit of the enzyme activity was identified as the enzyme amount to produce 1 µmol of epilactose from lactose per 1 minute at the above condition.

One of the cellobiose 2-epimerase proteins of the present invention may have amino acid sequence of SEQ ID NO:1 in its N-terminal, in addition to the above physicochemical properties.

The cellobiose 2-epimerases of the present invention usually have a specific amino acid sequence, for example, amino acid sequence of SEQ ID NO:10 or those homologous to SEQ ID NO:10.

The amino-acid sequences homologous to SEQ ID NO:10 encompasses amino acid sequences where one or more but less than 10 amino acid residues in SEQ ID NO:10 are deleted, replaced or added deleing, replacing or adding with other amino acid sequence, as long as the above enzymatic activities of catalyzing the sorts of epimerization.

The "DNA of the present invention" means a DNA encoding cellobiose 2-epimerase protein with the above amino-acid sequence.

The DNA of the present invention is not restricted to either native one or artificial one so long as it encodes the cellobiose 2-epimerase. As native DNA sources, microorganisms in the genus *Caldicellusiruptor* including *Caldicellusiruptor saccharolyticus* ATCC43494 are used, and a genomic DNA containing the DNA of the present invention can be obtained from these microbial cells. The microorganisms are inoculated in a nutrient culture medium, anaerobically cultured for about one to three days, and then the cells collected from the culture broth are treated with a cell wall lytic enzyme such as lysozyme or β-glucanase or with ultrasonic disruption to elute a genomic DNA containing the DNA of the present invention. In the above method, treatment with proteolytic enzyme such as protease, addition of surfactant such as SDS, or freezing-thawing treatment can be used in combination with the above process. The resultant solution is further treated by conventional method such as, for example, by extraction with phenol, precipitation with alcohol, centrifugation, treatment with ribonuclease, to obtain the objective genomic DNA. An artificial DNA of the present invention can be chemically synthesized according to the amino acid sequence of SEQ ID NO:10. It can be also synthesized by PCR method, using a chemically-synthesized oligonucleotide as a primer and the genomic DNA containing the DNA of the present invention as a template.

The DNA of the present invention may have the specific nucleotide sequence, for example, nucleotide sequence of SEQ ID NO:9, those homologous or complementary to SEQ ID NO:9. The nucleotide sequences homologous to SEQ ID NO:9 encompass nucleotide sequences where one or more but less than 30 nucleotides in SEQ ID NO: 9 are deleted, replaced or added with other nucleotide, as long as the activities of the encoding enzymes are remained.

As is obvious, the DNA of the present invention also encompasses DAN having nucleotide sequenced homologous to SEQ ID NO:9 or those where one or more but less than 30 nucleotides in SEQ ID NO:9 are deleted, replaced or added with other nucleotides with remaining the enzyme activity, in which further one or two nucleotides are replaced with other nucleotides without altering the encoding amino acids according to degeneracy.

The DNA of the present invention can be advantageously inserted into an autonomously replicable vector to form a recombinant DNA. The recombinant DNA, which usually consists of an objective DNA and an autonomously replicable vector, can easily to be prepared by conventional DNA-recombinant technique, as long as the objective DNA is isolated. The vectors encompasses plasmid vectors such as pBR322, pUC18, pBluescript II SK(+), pUB110, pTZ4, pC194, pCR-Script Cam SK+, pHV14, TRp7, YEp7 and pBS7, phage vectors such as λgt·λC, λgt·λB, ρ11, φ1 and φ105.

Among them, pBR322, pUC18, pBluescript II SK(+), pCR-Script Cam SK+, λgt·λC and λgt·λB are suitable for expressing the DNA of the present invention in *Escherichia coli*, and pUB110, pTZ4, pC194, ρ11, φ1 and φ105 are suitable for expressing the DNA of the present invention in *Bacillus subtilis*. pHV14, TRp7, YEp7 and pBS7, are suitable for replicating the recombinant DNA in two or more hosts. The objective DNA can be inserted into a vector by conventional method in the field of the art.

Concretely, the genomic DNA containing the objective DNA and an autonomously replicable vector are digested into fragments by a restriction enzyme, and obtained DNA fragments and vector fragments are ligated. When restriction enzymes used to digest the genomic DNA or the vector are those specific to nucleotides, particularly, type II restriction enzymes such as Sau 3AI, EoRI, Hind III, Bam HI, Sal I, Xba I, Sac I, Pst I, Nde I or Nco I, the DNA fragments and the vector fragments can be easily ligated.

When needed, both fragments are annealed before subjected to the action of DNA ligase intracellularly or extracellularly.

The recombinant DNA obtained by the above method is introduced into a host, and can be infinitely replicated by culturing the transformant.

The recombinant DNA obtained by the above method can be introduced into a host microorganism such as *Escherichia coli*, *Bacillus subtilis*, actinomycete or yeast to give a transformant.

The transformant can be obtained by colony hybridization method or selecting strains producing the cellobiose 2-epimerase activity in the crude enzyme prepared from the nutrient culture broth of the cells.

The media for culturing the microorganisms producing the cellobiose 2-epimerase of the present invention (including transformants) are not restricted in either synthetic media or natural media so long as the microorganism can grow and produce the cellobiose 2-epimerase in the medium. As the carbon source, compounds utilized by the microorganism can be used, for example, saccharides such as partial-starch hydrolysate, glucose, fructose, lactose, sucrose, mannnitol, sorbitol and molasses, organic acids such as citric acid and succinic acid. The concentration of the carbon source can be arbitrarily determined according to the medium. As the nitrogen source, inorganic nitrogen compounds such as ammonium salts and Nitrate salts, and organic nitrogen compounds such as urea, corn steep liquor, casein, peptone, yeast extract and meat extract, for example, can be used. Salts such as calcium salts, magnesium salts, potassium salts, sodium salts, phosphoric salts, manganese salts, zinc salts, iron salts, copper salts, molybdenum salts and cobalt salts can be used as inorganic ingredients. If necessary, amino acids or vitamins can be arbitrarily used.

The microorganism producing the cellobiose 2-epimerase of the present invention is cultured under a suitable condition for growth. For example, a microorganism in the genus of *Caldicellusiruptor* is usually cultured at a temperature of 50 to 80° C., preferably 60 to 70° C., at pH 5 to 8, preferably pH 6.5 to 7.5 under anaerobic condition. The culturing time is not restricted as long as the microorganism can grow, preferably for 10 to 72 hours. When a transformant is used, although the culture condition is different according to the kind of the host, it can be usually cultured at a temperature of 15 to 37° C. and pH 5.5 to 10, preferably at a temperature of 20 to 50° C. and pH 2 to 9 under aerobic condition with aeration and agitation, for 10 to 150 hours. The culturing method can be batch-wise or continuous.

After the microorganism was cultured by the above method, the culture broth containing the cellobiose 2-epimerase of the present invention is collected. Since the major activity of the cellobiose 2-epimerase is detected inside the microbial cells, the crude enzyme can be obtained in a form of the microbial cells themselves or the disrupted cell extract. The microbial cells are collected from the culture broth by conventional solid-liquid separation method. As the separation method, centrifugation of the culture broth, filtration with pre-coated filter or membrane filtration with flat membrane or hollow-fiber membrane. Even though the disrupted cell extract can be used as the crude enzyme without modification, it is usually used after concentrated. As the concentration method, ammonium sulfate fractionation, acetone or alcohol precipitation or membrane concentration with flat membrane or hollow-fiber membrane can be used.

When the cellobiose 2-epimerase of the present invention is a recombinant enzyme, it may be accumulated in the microbial cells depending on the kind of microorganism. In that case, although the cells or culture broth can be used as the enzyme without modification, usually, the recombinant enzyme isolated from the cell or the disrupted cells are advantageously used, which is extracted from the cells by hyperosmotic shock or with surfactant, or separated from the cells by filtration or centrifugation after disrupted by ultrasonication or treated with cell wall lytic enzyme.

As described above, even though the cellobiose 2-epimerase of the present invention can be the crude enzyme that is the disrupted cell extract without modification or its concentration, it can be further separated or purified by conventional method if necessary. For example, the supernatant of the disrupted cell extract is concentrated with UF membrane or fractionated with ammonium sulfate followed by dialysis, and then the obtained enzyme solution was purified by combination of purification methods such as anion-exchange chromatography, hydrophobic chromatography, gel-filtration chromatography, to obtain the purified cellobiose 2-epimerase of the present invention as an electrophoretically single protein. When the cellobiose 2-epimerase of the present invention is the recombinant one obtained by culturing the transformant, after the crude enzyme, obtained from the disrupted cell extract by ammonium sulfate fractionation and concentration, is heated at about 70° C. for certain period to denature the impurity proteins from the host, the enzyme can be easily purified by removing the precipitating denatured proteins by centrifugation, because the enzyme is more thermostable than other general proteins.

Furthermore, the cellobiose 2-epimerase of the present invention can be made into an immobilized enzyme prepared from the disrupted cell extract having the cellobiose 2-epimerase activity, its concentrated solution or the purified enzyme solution. The enzyme can be immobilized by binding to ion-exchanging material, adsorbing or covalently binding to resin or membrane, or embedding into polymer.

The cellobiose 2-epimerase of the present invention has wide substrate specificity. As shown in the experiments described below, the enzyme acts on D-glucose, D-galactose and D-mannose among monosaccharides to convert them into the corresponding epimers, i.e., D-mannose, D-talose and D-glucose, respectively. The enzyme acts on maltose, cellobiose and lactose among disaccharides to convert them into epimaltose, epicellobiose and epilactose, respectively. Furthermore, the enzyme acts on cellooligosaccharides and maltooligosaccharides among oligosaccharides to convert them into epicellooligosaccharides and epimaltooligosaccharides, respectively.

The cellobiose 2-epimerase of the present invention can catalyze aldose-ketose conversion as well as 2-epimerization when large amount of the enzyme is used. The enzyme can convert D-glucose or D-mannose into D-fructose, and D-galactose or D-talose into D-tagatose among monosaccharides. The enzyme can convert cellobiose or epicellobiose into cellobiulose, lactose or epilactose into lactulose, and maltose or epimaltose into maltulose among disaccharides. Although the enzyme converts aldose into ketose and also catalyses its reverse reaction, the activity of converting ketose into aldose is so weak that a large amount of the enzyme is required for the reverse reaction.

When the cellobiose 2-epimerase of the present invention is allowed to act on a substrate, the substrate concentration is not restricted. Even when the concentration of substrate solution is relatively low, for example, 0.1% (w/v), the reaction by the cellobiose 2-epimerase of the present invention can proceed and a saccharide as the substrate is converted into its epimer or isomer by aldose-ketose conversion. In industrial scale, the substrate concentration is preferable to be 1% (w/v) or more, and under the condition, various epimers and/or isomers can be advantageously produced. The reaction temperature can be a temperature at which the reaction can proceed, i.e., up to about 80° C., preferably, about 50 to 60° C. The reaction pH is usually adjusted in pH 5.0 to 9.0, preferably, 6.0 to 8.0. The usage of the enzyme, closely related to the reaction time, is determined according to the progress of the enzyme reaction.

Isomerized saccharides can be prepared by culturing a microorganism producing the cellobiose epimerase of the present invention in a nutrient culture medium containing the above aldose or ketose as the substrate and collecting the corresponding isomerized saccharides produced in the culture broth.

As the purification method of the isomerized saccharides obtained by the above methods, one or more conventional methods generally used for purification of saccharides, described as follows are feasible: for example, decolorizing with activated charcoal, deionization with H— or HO— from ion-exchange resin, fractionation by column chromatography such as ion-exchange column chromatography, activated-carbon column chromatography and silica-gel column chromatography, separation with membrane having suitable separating function, fermentation treatment using a microorganism such as yeast that utilizes or decomposes the impurity saccharides but not the objective saccharides, and enzyme treatment using an enzyme that specifically decompose the material saccharides but not the objective saccharides.

Particularly, as industrial purification method, ion-exchange column chromatography is preferable. For example, by removing impurity saccharides by column chromatography using strong acid cation exchange resin described in Japanese Patent Kokai No. 23799/1983 or Japanese Patent Kokai No. 72598/1983, saccharide composition with higher content of the objective saccharide can be advantageously prepared. For the above chromatography, fixed bed method, moving bed method and simulated moving bed method can be used.

The present invention is more concretely explained by the following experiments.

Experiment 1

Production of Epilactose and Epicellobiose by Extract of Disrupted Cells of *Caldicellusiruptor saccharolyticus* ATCC43494

Experiment 1-1

Culture of *Caldicellusiruptor saccharolyticus* ATCC43494 and Preparation of its Extract of Disrupted Cells American Type Culture Collection Medium No. 1368, described in "ATCC Catalogue of American Type Culture Collection the 18th ed.", pp. 470, published by American Type Culture Collection, 1992, was prepared, and 12 ml of the medium was put into a 12-ml pressure glass bottle and sterilized. *Caldicellusiruptor saccharolyticus* ATCC43494 was inoculated in the medium and statically cultured at 70° C. for about 72 hours. The obtained cells were separated from the culture broth by centrifugation and disrupted by ultrasonication, and the supernatant separated from the disrupted cell extract by centrifugation is obtained as a crude enzyme solution.

Experiment 1-2

Acton of Crude Enzyme Solution on Lactose, Cellobiose and Epilactose

Cellobiose, lactose or epilactose was dissolved in 100 mM acetate buffer (pH 6.0) at the final concentration of 3.4% (w/w) to give substrate solutions of each saccharide. Ten µl of the substrate solution was admixed with 10 µl of the crude enzyme solution prepared by the method of Experiment 1, and reacted at 50° C. for 16 hours. After the reaction, the resultant solution was subjected to thin-layer chromatography (hereinafter, abbreviated in "TLC") carried out in the following condition.

The results were in FIG. 1.

TLC Analytical Condition

TLC plate: "KIESELGEL 60 $F_{254}$" (produced by Merck KGaA, Germany, 10×20 cm size)

Developing solvent: mixture of n-butanol:pyridin:water (6:4:1, v/v)

Developing method: ascending method, twice

Detection: spraying 10% sulfuric acid-methanol followed by heating at 110° C. for 6 minutes The symbols "a" to "g" in FIG. 1 mean the samples subjected to TLC; "a", "b", "c", "d", "e", "f" and "g" symbolize mixture of maltooligosaccharides (marker of glucose polymerization degree), cellobiose reference standard, reaction mixture of cellobiose, lactose reference standard, reaction mixture of lactose, epilactose reference standard and reaction mixture of epilactose, respectively. As shown in FIG. 1, spots of glucose ("$G_1$" of "a" in FIG. 1), a cellobiose degradation product, and unknown saccharide ("e" in FIG. 1) were recognized in the reaction mixture of cellobiose ("c" in FIG. 1), and spots of glucose and galactose ("$G_2$" of "a" in FIG. 1), lactose degradation products, were recognized in the reaction mixture of lactose ("e" in FIG. 1). On the other hand, a spot of an isomerized product ("←" in FIG. 1), that is presumable lactose, was recognized in the reaction mixture of epilactose ("g" in FIG. 1). Since lactose, an isomer of epilactose, was found in the reaction mixture of epilactose, it was considered that also in the reaction mixture of cellobiose or lactose, some products other than their decomposition products might be produced, but their spots overlapped with the decomposition products. And so, the reaction mixture of cellobiose or lactose were subjected to trimethylsilyl (TMS) derivatization by conventional method, and then subjected to gas chromatography (hereinafter, abbreviated as "GC") under the following condition to identify the products. As the results, it was revealed that epilactose was formed from lactose and presumable epicellobiose was formed from cellobiose, besides the degradation products. These results indicate that *Caldicellusiruptor saccharolyticus* ATCC43494 produces cellobiose 2-epimerase, an epimerase that epimerizes cellobiose, lactose, and epilactose.

GC Analytical Condition

GC device: GC-14A (produced by Shimadzu Corporation, Kyoto, Japan)

Column: 2% OV-17 Chromosorb W/AW-DMCS (3 mm in ID×2 m in length, produced by GL Science Inc., Tokyo, Japan)

Carrier gas: Nitrogen
Carrier gas flow rate: 40 ml/min
Combustion gas: hydrogen
Combustion gas flow rate: 40 ml/min
Supporting gas: Air
Supporting gas flow rate: 600 ml/min
Temperature rising: 160° C.→320° C. (7.5° C./min)
Detection: FID (hydrogen flame ionization detector)

Experiment 2

Purification of Cellobiose 2-Epimerase from *Caldicellusiruptor saccharolyticus* ATCC43494

To reveal the physicochemical properties of the cellobiose 2-epimerase produced by *Caldicellusiruptor saccharolyticus* ATCC43494, the enzyme was purified.

Experiment 2-1

Preparation of Crude Enzyme

*Caldicellusiruptor saccharolyticus* ATCC43494 was cultured by the same method of Experiment 1-1 except for the cells were inoculated into 100 ml of the medium used in Experiment 1-1 eight each in eight 100-ml pressure glass bottles, as the seed culture.

Then, each seed culture broth was inoculated into 10 L of the same medium eight each in eight 11-L pressure steel bottles and cultured. After cultured, total about 80 L of the culture broth was centrifuged and 24 g of wet cells were collected. The cells were suspended in 20 mM Tris-HCl buffer (pH 7.5), disrupted by ultrasonication, and the supernatant of the disrupted cell extract was obtained as the crude enzyme. The epimerase activity of the crude enzyme was determined to be 0.009 Unit/ml.

Experiment 2-2

Purification of Cellobiose 2-Epimerase

The crude enzyme obtained in Experiment 2-2 was concentrated with UF membrane and the resultant concentrated enzyme solution in a volume of 40 ml was collected. The concentrated enzyme solution was dialyzed against 20 mM Tris-HCl buffer (pH 7.5) overnight and the dialyzed solution was centrifuged to remove the sediments. The resultant supernatant (38 ml) was subjected to anion exchange chromatography using "DEAE-TOYOPESRL 650S" gel (commercialized by Tosoh Corporation, Tokyo, Japan) in a gel volume of 380 ml. The adsorbed proteins were eluted by linear gradient of 0 to 0.5M NaCl. The epimerase activity of each fraction was measured and it was revealed that the epimerase activity was eluted in the about 0.1M-NaCl fraction. The active fraction was collected and after dialyzed against the same buffer containing 1M ammonium sulfate, subjected to hydrophobic column chromatography using "Butyl-TOYOPERL 650M" (commercialized by Tosoh Corporation, Tokyo, Japan) in a gel volume of 50 ml. The adsorbed proteins were eluted by linear gradient of 1 to 0 M ammonium sulfate. The epimerase activity was eluted in the about 0.8-M ammonium sulfate fraction. The active fraction was concentrated with UF membrane, dialyzed against 20 mM Tris-HCL buffer (pH 7.5), and subjected to gel chromatography using "SUPERDEX 75" column (16 mm×60 cm, produced by GE Healthcare Bioscience Japan, Tokyo, Japan) pre-equilibrated with the same buffer, and the fraction having the epimerase activity was collected. The active fraction was dialyzed against 20 mM Tris-HCL buffer (pH 7.5) overnight, and subjected to anion exchange chromatography using "DEAE-5PW" column (3.3 ml, produced by Tosoh Corporation, Tokyo, Japan) pre-equilibrated with the same buffer. The adsorbed proteins were eluted by linear gradient of 0 to 0.5 M NaCl and the about 0.1 M-NaCl fraction having the epimerase activity was collected.

The enzyme preparation purified by the above process contained 0.9 mg protein, and its activity yield was 3.4% from the crude enzyme. The specific activity of the purified enzyme preparation was 26.9 unit/mg-protein. The amount of protein was measured by Lowry method using bovine serum albumin as standard.

The purity of the purified enzyme preparation was analyzed by polyacrylamide gel electrophoresis with concentration gradient of 5 to 20% (w/v). The resultant protein band was single, revealing that the purified enzyme preparation was of high purity.

Experiment 3

Properties of Cellobiose 2-Epimerase from *Caldicellusiruptor saccharolyticus* ATCC43494

Experiment 3-1

Molecular Weight

The purified cellobiose 2-epimerase preparation obtained by the method of Experiment 2 was analyzed by SDS-polyacrylamide gel electrophoresis with concentration gradient in a range of 5 to 20% (w/v). The molecular weight of the enzyme was determined by comparing the molecular-weight marker (produced by Nippon Bio-Rad Japan, Tokyo, Japan) electrophoresed at the same time, resulting in 4,000±5,000 daltons.

Experiment 3-2

Optimum Temperature and Optimum pH

Figure 3:
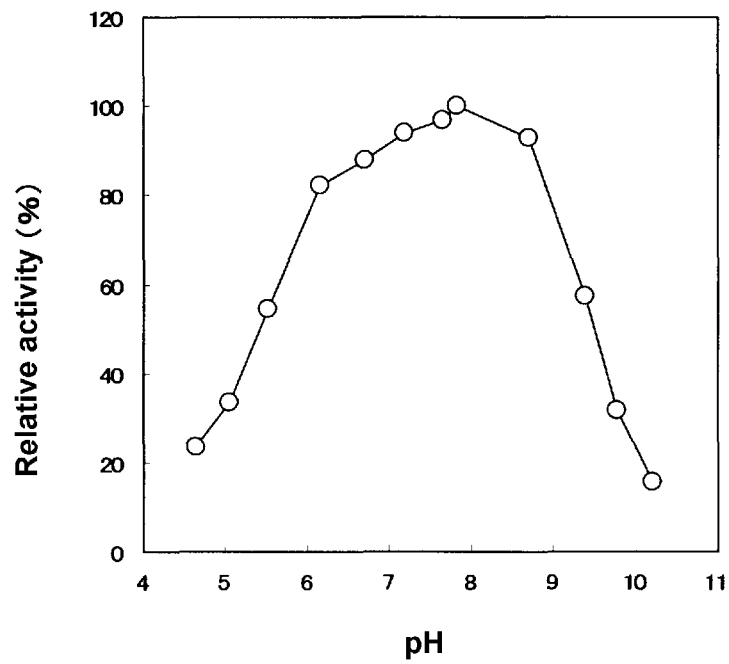
FIG. 3 shows the effect of pH on the cellobiose 2-epimerase activity of the present invention.
Figure 4:
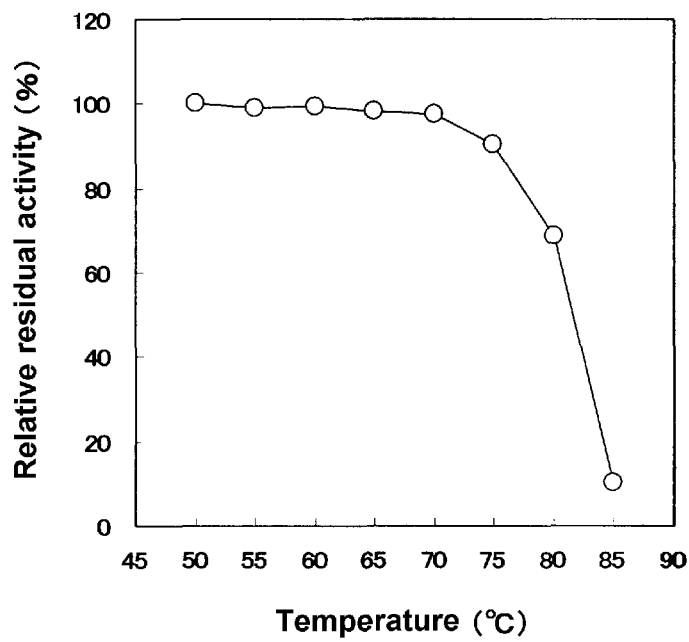
FIG. 4 shows the effect of temperature on the stability of the cellobiose 2-epimerase of the present invention.

Using the purified cellobiose 2-epimerase preparation obtained by the method of Experiment 2, effects of temperature and pH on the epimerase activity were investigated according to the method of assaying the activity. The results were in FIG. 3 (optimum temperature) and FIG. 4 (optimum pH). The optimum temperature of the enzyme is 80° C. when reacted at pH 6.0 for 20 minutes. The optimum pH of the enzyme is 7.8 when reacted at 50° C. for 20 minutes.

Experiment 3-3

Thermostability and pH Stability

Using the purified cellobiose 2-epimerase preparation obtained by the method of Experiment 2, effects of temperature and pH on stability of the epimerase activity were investigated.

Figure 5:
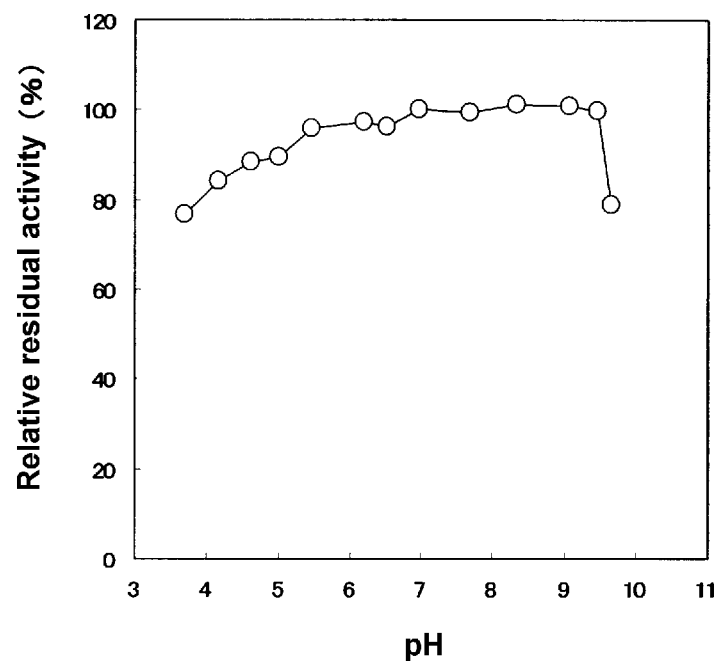
FIG. 5 shows the effect of pH on the stability of the cellobiose 2-epimerase of the present invention.

The thermostability was determined as the residual activity of the enzyme, after incubated at given temperatures for 60 minutes in 10 mM acetate buffer (pH 6.0) followed by being cooled in cold water. The pH stability was determined as the residual activity of the enzyme, after incubated at 4° C. for 24 hours in 10 mM acetate buffer of given pHs. The results were in FIG. 5 (thermostability) and FIG. 6 (pH stability). As shown in FIG. 5, the epimerase was stable at a temperature up to 70° C.

As shown in FIG. 6, the epimerase was stable in a pH range of 4.5 to 9.5.

Experiment 3-4

Effect of Metal Ions on the Epimerase Activity

Using the purified cellobiose 2-epimerase preparation obtained by the method of Experiment 2, effects of metal ions on the enzyme activity were investigated by assaying the activity in the presence of given metal ion at the concentration of 1 mM. The results were in Table 1.

TABLE 1

| Metal salt | Relative activity (%) | Metal salt | Relative activity (%) |
|---|---|---|---|
| None | 100 | $CuCl_2$ | 1 |
| $MgCl_2$ | 106 | $ZnCl_2$ | 1 |
| $AlCl_3$ | 45 | $SrCl_2$ | 104 |
| $CaCl_2$ | 107 | $BaCl_2$ | 108 |
| $MnCl_2$ | 104 | $HgCl_2$ | 1 |
| $FeCl_2$ | 35 | $PbCl_2$ | 36 |
| $FeCl_3$ | 33 | EDTA | 99 |
| $CoCl_2$ | 101 | Tris | 93 |
| $NiCl_2$ | 103 | | |

As shown in Table 1, the activity of the epimerase was inhibited by $Al^{3+}$, $Fe^{2+}$, $Fe^{3+}$ and $Pb^{2+}$, and almost completely inhibited by $Cu^{2+}$, $Zn^{2+}$ and $Hg^{2+}$.

Experiment 3-5

N-Terminus Amino Acid Sequence

Using the purified cellobiose 2-epimerase preparation obtained by the method of Experiment 2, the N-terminus amino acid sequence of N-terminal to 15th amino acid residues in the enzyme was analyzed with "PROTEIN SEQUENCOR Model 492HT" (produced by Applied Biosystems Japan, Tokyo, Japan), and it was revealed that the N-terminus amino acid sequence of the enzyme was amino acid sequence of SEQ ID NO:1, i.e., methionine-aspartic acid-isoleucine-threonine-arginine-phenylalanine-lysine-glutamic acid-aspartic acid-leucine-lysine-alanine-histidine-leucine-glutamic acid.

Experiment 3-6

Internal Amino-Acid Sequence

Adequate amount of the purified cellobiose 2-epimerase preparation obtained by the method of Experiment 2 was dialyzed against 10 mM Tris-HCl buffer (pH 9.0) at 4° C. for 18 hours, and then diluted with the same buffer to give protein concentration of about 0.6 mg/ml. Fifty µl of the resultant solution was admixed with 1.2 µg of lysylendopeptidase (commercialized by Wako Pure Chemical Industries, Ltd., Tokyo, Japan) and incubated at 30° C. for 20 hours to hydrolyze the enzyme protein. The resultant hydrolyzate was injected into HPLC column "MicroPCR C2/C18 SC2.1/10" (2.1 mm in ID×100 mm in length produced by GE Healthcare Bioscience Japan, Tokyo, Japan) preliminarily equilibrated with 0.065% (v/v) trifluoroacetic acid, and the peptide fragments were fractionated by elution with 160-minute linear gradient of 0.065% (v/v) trifluoroacetic acid to 0.055% (v/v) trifluoroacetic acid in 80% (v/v) acetonitrile solution at a flow rate of 0.1 ml/min under ambient temperature. The peptide fragments in the eluent were detected by measuring the absorbance at 214 nm. Three peptide fragments, P1, P2 and P3, which were eluted at the retention time of about 29, 37 and 39 minutes, respectively, were collected and their amino-acid sequences were analyzed by the same method of Experiment 3-5, and it was found that they have amino acid sequences of SEQ ID NO:2, SEQ ID NO:3 and SEQ ID NO:4, respectively.

Experiment 4

Cloning of DNA Encoding Cellobiose 2-Epimerase and Preparation of its Recombinant DNA and its Transformant The DNA encoding the cellobiose 2-epimerase was cloned from *Caldicellusiruptor saccharolyticus* ATCC43494 and its autonomously replicable recombinant DNA was prepared. And then, the DNA nucleotide sequence encoding the enzyme was determined and its transformant was prepared.

Experiment 4-1

Preparation of Genomic DNA

*Caldicellusiruptor saccharolyticus* ATCC43494 was cultured by the same method of Experiment 1-1, and the cells were collected from 20 ml of the culture solution by centrifugation. A genomic DNA was prepared from the collected cells according to the method described in the instruction attached to "DNeasy Tissue Kit" (produced by QIAGEN Japan, Tokyo, Japan). Its yield was 1.8 mg. The concentration of the genomic DNA solution was adjusted to 1.8 mg/ml.

Experiment 4-2

Cloning the DNA Encoding the Cellobiose 2-Epimerase and Determination of its DNA Base Sequence According to the sequence from the N-terminal to the sixth amino acid residues of the N-terminus amino acid sequence (SEQ ID No:1) of the cellobiose 2-epimerase, a nucleotide having nucleotide sequence of SEQ ID NO:5 was synthesized as a sense primer. According to the sequence from the second to seventh amino acid residues of amino acid sequence of SEQ ID NO:4, an internal amino acid sequence of the epimerase, a nucleotide having nucleotide sequence of SEQ ID NO:6 was synthesized as an antisense primer. Using these primers, the genomic DNA obtained in Experiment 4-1 as the template, and KOD-Plus-DNA polymerase (produced by Toyobo Co., Ltd., Tokyo, Japan) as PCR enzyme, the DNA was amplified by conventional PCR method using "DNA THERMAL CYCLER PJ2000" (produced by Perkin-Elmer Japan Co., Ltd., Kanagawa, Japan), and an about 1,000-bp DNA fragment was amplified. The DNA fragment was cloned at the restriction-enzyme Srf I site of "pCR-Script Cam SK+" (a cloning vector produced by Stratagene, Agilent Technologies, USA) and *E. coli* XL-10 Gol was transformed by the obtained recombinant DNA. The plasmid of the transformant had the objective about 1,000-bp DNA fragment. The recombinant DNA was named as "pCRCS1".

The nucleotide sequence of the about 1,000-bp DNA fragment of the recombinant DNA, "pCRCS1", was decoded by conventional dideoxy method. The amino acid sequence encoded by interpretation of the 1,004-bp nucleotide sequence included an internal amino-acid sequence of the cellobiose 2-epimerase (amino-acid sequence of SEQ ID NO:3). These results suggested that the obtained DNA fragment was a part of the DNA encoding the objective cellobiose 2-epimerase.

After confirming the above DNA fragment deemed as a part of the DNA encoding the cellobiose 2-epimerase was not digested by restriction enzyme Pst I, the genomic DNA obtained in Experiment 4-1 was digested with the restriction enzyme Pst I and the resultant digest was allowed to self-ligate to form a circular genome.

According to the nucleotide sequence of the DNA fragment deemed as a part of the DNA encoding the cellobiose 2-epimerase, oligonucleotides having nucleotide sequences of SEQ ID NO:7 and SEQ ID NO: 8 were synthesized as a sense primer and an antisense primer, respectively, and then the DNA was amplified by PCR using the above circular genome as the template. An about 3,400-bp amplified DNA fragment was obtained.

The obtained 3,400-bp DNA fragment was directly decoded by conventional dideoxy method, and the open reading frame encoding amino acid sequence including the N-terminus amino acid sequence of the cellobiose 2-epimerase (amino acid sequence of SEQ ID NO:1) and three internal amino acid sequences (amino-acid sequences of SEQ ID NO:2 to SEQ ID NO:4) was found. It means that the DNA fragment had the whole objective gene. Based on the above finding, the nucleotide sequence of the DNA encoding the cellobiose 2-epimerase and the amino acid sequence encoded thereby were determined. It was found that the DNA encoding the cellobiose 2-epimerase of *Caldicellusiruptor saccharolyticus* ATCC43494 has nucleotide sequence of SEQ ID NO:9 with 1,170 bp and it encodes amino acid sequence of SEQ ID NO:10 with 390 amino acid residues. The N-terminus amino acid sequence (SEQ ID NO:1) determined in Experiment 3-5 and three internal amino acid sequences (SEQ ID NO:2 to SEQ ID NO:4) determined in Experiment 3-6 were all included in amino acid sequence of SEQ ID NO:10 and they exactly corresponded to the sequence of first to 15th amino acid residues, 342nd to 349th amino acid residues, 104th to 110th amino acid residues, and 329th to 335th amino acid residues in SEQ ID NO:10, respectively.

The molecular weight was calculated to be 46,488 daltons from the amino acid sequence of SEQ ID NO:10, and it well agreed with 44,000±5,000 daltons, the molecular weight of the cellobiose 2-epimerase of *Caldicellusiruptor saccharolyticus* ATCC43494 determined in Experiment 3-1.

Experiment 4-3

Construction of a Recombinant DNA Vector for Expressing a Recombinant Cellobiose 2-Epimerase and Preparation of a Transformant Based on the 1st to 9th amino acid sequences in SEQ ID NO:1, the N-terminus amino acid sequence of cellobiose 2-epimerase from *Caldicellulosiruptor saccharolyticus* ATCC43494, and to make a restriction enzyme Nco I site at the 5'-terminus of the gene, an oligonucleotide having the nucleotide sequence of SEQ ID NO:11 was synthesized as a sense primer.

Further, based on the 384th to 390th amino acid sequences in SEQ ID NO:10, and to make a restriction enzyme Bam HI site at the 3'-terminus of the gene, an oligonucleotide having the nucleotide sequence of SEQ ID NO:12 was synthesized as an antisense primer. A PCR-amplification was carried out by conventional method using the primers, the genomic DNA obtained in Experiment 4-1 as a template, and "KOD-Plus-DNA-Polymerase", commercialized by Toyobo Co., Ltd., Tokyo, Japan, as a PCR enzyme, by using "DNA THERMAL CYCLER PJ2000", a PCR apparatus commercialized by Perkin-Elmer Japan Co., Ltd., Kanagawa, Japan.

As the result, a 1,200 bp-DNA fragment was amplified. The amplified DNA fragment was digested by restriction enzymes, Nco I and Bam HI, and after the restriction enzymes were inactivated by phenol-chloroform method, the resulting DNA fragment was inserted into an expression vector, pET-3d, commercialized by Novagen, Merck KGaA, Germany, pre-digested by restriction enzymes, Nco I and Bam HI, using "LIGATION HIGHT", a kit commercialized by Toyobo Co., Ltd., Tokyo, Japan. Then, "XL10-Gold", a host *E. coli* for cloning commercialized by Stratagene, Agilent Technologies, USA, was transformed using the reaction mixture. Plasmids were prepared by the transformants, and a transformant having the objective 1,200 bp-DNA fragment in the plasmid was selected. The recombinant DNA in the selected transformant was named as "pETCS1", and then a transformant "ETCS1", was prepared by transforming *E. coli* Rosetta (DE3), *E. coli* for gene expression commercialized by Novagen, Merck KGaA, Germany, using the recombinant DNA, pETC1.

Experiment 4-4

Expression of a Recombinant Cellobiose 2-Epimerase in a Transformant, and the Purification of the Enzyme A transformant, ETCS1, obtained in Experiment 4-3, was inoculated into TB medium containing 1.2% tryptone, 2.4% yeast extract, 0.4% glycerol, 17 mM potassium hydrogen phosphate, 72 mM di-potassium hydrogen phosphate, pH 6.8, 80 µg/ml of ampicillin, and 30 µg/ml chloramphenicol; placed in a 500 ml-Erlenmeyer flask in respective amount of 100 ml and cultured at 27° C. for 24 hours. The resulting culture broth was centrifuged by conventional method and cells and supernatant were collected separately. In the case of the cells, whole-cell extract was prepared by ultrasonic disruption. The ultrasonic disruption was carried out by suspending cells in 20 mM acetate buffer (pH6.5) and disrupting cells in suspension in an ice bath using a ultrasonic homogenizer, "Model UH-600", commercialized by MST Corporation, Aichi, Japan, and the resulting homogenate was used as a whole-cell extract.

The cellobiose 2-epimerase activities (as lactose 2-epimerase activities) of the culture supernatant and whole-cell extract, prepared as described above, were assayed, and those values were expressed in terms of the activities/ml-culture, respectively. As a control, E. coli Rosetta (DE3), having a plasmid, pET-3d, was cultured by the same conditions as the above transformant, and the culture supernatant and the whole-cell extract were prepared and assayed in the same manner. The results are in Table 2.

TABLE 2

| Strain | Cellobiose 2-epimerase activity* (units/ml-broth) | |
|---|---|---|
| | Culture supernatant | Whole cell extract |
| ETCS1 (The present invention) | 0.0 | 25.4 |
| E. coli Rosetta (DE3) pET-3d (Control) | 0.0 | 0.0 |

*Lactose 2-epimerase activity

As is evident from the results in Table 2, it was revealed that the transformant, ETCS1 produced cellobiose 2-epimerase intracellularly. In the case of the host, E. coli, no epimerase activity was detected in both of the culture supernatant and the whole-cell extract.

The whole-cell extract, obtained above, was heated at 70° C. for 30 min, and the resulting denatured and aggregated proteins which were originated from the host were removed by centrifugation. The supernatant obtained by the heat treatment was further purified by an anion exchange chromatography using "DEAF-5PW" column and a successive gel filtration chromatography using "SUPERDEX 200" gel, and the purified enzyme preparation was analyzed according to the methods in Experiment 3. As a result, the molecular weight was about 44,000±5,000 daltons by SDS-polyacrylamide gel electrophoresis; the optimum temperature of epimerase activity was about 80° C. when reacted at pH 6.0 for 20 min; the optimum pH of the enzyme was about 7.8 when reacted at 50° C. for 20 min; the thermal stability was up to about 70° C. when incubated at various temperatures for 60 min; and the pH stability was in the range of about pH 4.5 to about 9.5 when incubated at various pHs at 4° C. for 24 hours. These physicochemical properties of the recombinant epimerase were substantially identical to those of the cellobiose 2-epimerase purified in Experiment 2. The above results indicate that cellobiose 2-epimerase from Caldicellulosiruptor saccharolyticus ATCC43494 can be advantageously produced by recombinant DNA technique.

Overall nucleotide sequence of the genomic DNA of Caldicellulosiruptor saccharolyticus ATCC43494 has been already determined and registered to "GenBank", a gene database with an accession No. CP000679. The present inventors searched the genomic DNA information based on SEQ ID NO:10, all amino acid sequence of the cellobiose 2-epimerase determined in Experiment 4-2 and it was unexpectedly revealed that the amino acid sequence of the cellobiose 2-epimerase is completely identical with a amino acid sequence encoded by Csac0294, a gene deduced to encode "N-acyl-glucosamine 2-epimerase" in the genomic DNA of Caldicellulosiruptor saccharolyticus ATCC43494. The result indicates that the gene, Csac0294, which is deduced to encode "N-acyl-glucosamine 2-epimerase" in the genomic DNA of Caldicellulosiruptor saccharolyticus ATCC43494, exactly encodes the cellobiose 2-epimerase.

Experiment 5

Substrate Specificity of Cellobiose 2-Epimerase

Substrate specificity of the enzyme was investigated by allowing the purified preparation of the recombinant cellobiose 2-epimerase, obtained by the method of Experiment 4-4, to act on various saccharides. Substrate solutions were prepared by dissolving D-glucose, D-xylose, D-allose, D-ribose, D-galactose, D-fructose, D-mannose, D-psicose, D-tagatose, L-sorbose, L-rhamnose, L-ribose, trehalose, kojibiose, nigerose, isomaltose, neotrehalose, gentiobiose, lactose, sucrose, maltulose, palatinose, maltose, maltotriose, maltotetraose, maltopentaose, maltohexaose, maltoheptaose, cellobiose, cellotriose, cellotetraose, selaginose, isomaltosyl-glucoside, isomaltotriose, panose, isopanose, erlose, maltitol, maltotriitol, methyl-α-glucoside, methyl-β-glucoside, D-glucosamine, D-galactosamine, D-glucuronic acid, N-acetyl-glucosamine, or N-acetyl-galactosamine into MOPS buffer (pH 8.0) to give a final concentration of 2% (w/w) of saccharide and 40 mM buffer.

Then, each of the resulting substrate solutions was further admixed with 500 units/g-substrate, on a dry solid basis, of the purified preparation of recombinant cellobiose 2-epimerase, obtained by the method in Experiment 4-4, and followed by the enzyme reaction at 60° C. for 24 hours. After stopping the reaction by heating the reaction mixture at 100° C. for 10 minutes, each reaction mixture was subjected to TLC analysis under the conditions in Experiment 1-2 to examine the saccharides in each mixture before and after the reaction. The substrate specificity of the enzyme was judged by investigating whether the spot of the reaction product except for the substrate is detected in the TLC chromatogram or not, and the degree of the strength of the visualized spot. The results are in Table 3.

TABLE 3

| Substrate | Action* | Substrate | Action* |
|---|---|---|---|
| D-Glucose | + | Maltotriose | + |
| D-Xylose | − | Maltotetraose | ± |
| D-Allose | − | Maltopentaose | ± |
| D-Ribose | − | Maltohexaose | ± |
| D-Galactose | ± | Maltoheptaose | ± |
| D-Fructose | ± | Cellobiose | ++ |
| D-Mannose | + | Cellotriose | ++ |
| D-Psicose | − | Cellotetraose | ++ |
| D-Tagatose | ± | Selaginose | − |
| L-Sorbose | − | Isomaltosyl-glucoside | − |
| L-Rhamnose | − | Isomaltotriose | − |
| L-Ribose | − | Panose | − |
| Trehalose | − | Isopanose | − |
| Kojibiose | − | Erlose | − |
| Nigerose | − | Maltitol | − |
| Isomaltose | − | Maltotriitol | − |
| Neotrehalose | − | Methyl-α-glucoside | − |
| Gentiobiose | − | Methyl-β-glucoside | − |
| Lactose | ++ | D-Glucosamine | − |
| Sucrose | − | D-Galactosamine | − |
| Maltulose | ± | D-Glucuronic acid | − |
| Palatinose | − | N-Acetyl-glucosamine | − |
| Maltose | + | N-Acetyl-galactosamine | − |

*The symbol, "−" means "No product is detected". The symbol, "±" means "Some products are slightly detected". The symbol, "+" means "Some products are detected". The symbol, "++" means "Some products are clearly detected".

As is evident from the results in Table 3, the enzyme of the present invention acted on lactose, cellobiose, cellotriose, and cellotetraose with relatively strong specificity, and acted on D-glucose, D-mannose, maltose, and maltotriose among the saccharides tested, and formed corresponding products deemed as isomerized saccharides. Further, the enzyme of the present invention slightly acted on D-galactose, D-fructose, D-tagatose, maltulose, maltotetraose, maltopentaose, maltohexaose, and maltoheptaose.

Experiment 6

Isomerized Saccharides Formed from Monosaccharides

Reaction products formed from D-glucose, D-galactose, and D-mannose by the action of the cellobiose 2-epimerase of the present invention were investigated. D-Glucose, D-galactose, or D-mannose was dissolved into 50 mM acetate buffer (pH 6.0) to give a final concentration of 20% (w/v) to make into a substrate solution. To 0.1 ml of the substrate solution, 130 units/g-solid substrate for D-glucose and D-mannose (0.1 ml as the enzyme solution), or 500 units/g-solid substrate for D-galactose (0.1 ml as the enzyme solution), of the purified preparation of the recombinant cellobiose 2-epimerase, obtained by the method in Experiment 4-4, was admixed; and followed the enzyme reaction at 60° C. for 48 hours.

After the completion of the reaction, reaction mixture was heated at 100° C. for 10 minutes to stop the reaction. Each reaction mixture was subjected to HPLC analysis for determining the product. HPLC analysis of the products in the reaction mixture was carried out under the following conditions for separating monosaccharides. The results are in Table 4.

<Conditions for HPLC Analysis>
Column: "MCI gel CK08EC", produced by Mitsubishi Chemical Corporation, Tokyo, Japan
Eluent: Deionized water
Column temperature: 75° C.
Flow rate: 0.6 ml/min
Detector: "RID-10A", a refractive index detector produced by Shimadzu Corporation, Kyoto, Japan

TABLE 4

| Substrate | Amount of enzyme (Units/g-substrate) | Product | Content (%, w/w) |
|---|---|---|---|
| D-Glucose | 130 | D-Mannose | 20.6 |
| | | D-Fructose | 3.8 |
| D-Galactose | 500 | D-Talose | 10.3 |
| | | D-Tagatose | 8.4 |
| D-Mannose | 130 | D-Glucose | 41.8 |
| | | D-Fructose | 5.1 |

As is evident from the results in Table 4, the cellobiose 2-epimerase of the present invention formed D-mannose and D-fructose from D-glucose; D-talose and D-tagatose form D-galactose; and D-glucose and D-fructose from D-mannose. The action on D-galactose of the enzyme was relatively weak than those on D-glucose and D-mannose. The enzyme catalyzed the conversion of D-glucose and D-galactose into the corresponding epimers, D-mannose and D-talose, and further catalyzed the formation of D-fructose and D-tagatose. From the results, it was revealed that the enzyme of the present invention catalyzes both 2-epimerization and aldose-ketose conversion.

Experiment 7

Isomerized Saccharides Formed from Lactose

In order to indentify isomerized saccharides formed from lactose by the action of the cellobiose 2-epimerase of the present invention, isomerized saccharides were isolated and subjected to the structural analysis.

Experiment 7-1

Preparation of Isomerized Saccharides from Lactose

To 200 ml of substrate solution prepared by dissolving lactose into 20 mM acetate buffer (pH 6.0) to give a final concentration of 1.1% (w/v), 130 units/g-solid substrate of the purified recombinant cellobiose 2-epimerase preparation (20 ml of the enzyme solution) obtained by the method in Experiment 4-4 was added, and followed the enzyme reaction at 50° C. for 8 hours. After the completion of the reaction, the reaction mixture was heated at 100° C. for 10 minutes to stop the reaction.

In order to determine the saccharides in the reaction mixture, TLC analysis under the conditions described in Experiment 1-2 and the following HPLC analysis were carried out.

<Conditions for HPLC Analysis>
Column: "MCI gel CK08EP", produced by Mitsubishi Chemical Corporation, Tokyo, Japan
Eluent: Deionized water
Column temperature: 75° C.
Flow rate: 0.6 ml/min
Detector: "RID-10A", a refractive index detector produced by Shimadzu Corporation, Kyoto, Japan In the TLC chromatogram of the reaction mixture, two kinds of isomerized saccharide were detected together with unreacted lactose. An isomerized saccharide, showing the same Rf value with that of epilactose, was named as "Isomerized saccharide A", and another isomerized saccharide, showing lower Rf value and being hardly separated from lactose, was named as "Isomerized saccharide B". Since the spot of Isomerized saccharide B was visualized by diphenylamine-aniline-phosphate reagent on the TLC plate, it was suggested that the saccharide contains ketose in the structure. The HPLC chromatogram of the reaction mixture is shown in FIG. 6. In the HPLC, Isomerized saccharides A and B were separated from lactose (represented by the symbol, "Lac", in FIG. 6), but not separated each other and detected as a mixture (represented by the symbol, "A+B", in FIG. 6). The saccharide composition of the reaction mixture was 52.7% (w/w) of lactose and 47.3% (w/w) of the mixture of Isomerized saccharides A and B.

Experiment 7-2

Isolation and Purification of Isomerized Saccharides A and B

As described above, Isomerized saccharides A and B can be separated each other by TLC but Isomerized saccharide B can not be separated from lactose, while Isomerized saccharides A and B can be separated from lactose by HPLC but Isomerized saccharides A and B can not be separated each other. Based on the knowledge, the inventors of the present invention tried firstly to obtain the mixture of Isomerized saccharides A and B by removing lactose using HPLC, and successively, tried to isolate Isomerized saccharides A and B, respectively, by a preparative TLC.

Experiment 7-2-1

Preparation of a Mixture of Isomerized Saccharides A and B by Preparative HPLC

Total 330 mg-solid of the reaction mixture obtained in Experiment 7-1 was divided to 80 parts and each part was subjected to HPLC described in Experiment 7-1 to obtain the mixture of Isomerized saccharides A and B. Each fraction containing Isomerized saccharide A or B was concentrated and dried, and finally 153 mg of a saccharide preparation which contains 98.7% (w/w) of the mixture and 1.3% (w/w) of monosaccharides was obtained.

Experiment 7-2-2

Isolation of Isomerized Saccharides A and B by Preparative TLC

Total 57.6 mg-solid of the saccharide preparation containing Isomerized saccharides A and B, obtained in Experiment 7-2-1, was subjected to TLC described in Experiment 1-2 and developed two times. Then, silica gel layers corresponding the Rf values of Isomerized saccharides A and B were separately scraped away from the TLC plate. According to the conventional method, Isomerized saccharides A and B were respectively extracted from the collected silica gel layer using deionized water, concentrated and dried, and 21.9 mg-solid of Isomerized saccharide A and 17.8 mg-solid of Isomerized saccharide B were obtained. A part of each preparation was subjected to GC analysis described in Experiment 1-2 to measure the purity. The purity of Isomerized saccharide A was 90.2% (w/w), and the preparation contained 9.8% (w/w) of monosaccharides. The purity of Isomerized saccharide B was 97.7% (w/w), and the preparation contained 2.3% (w/w) of monosaccharides.

Experiment 7-3

Structural Analyses of Isomerized Saccharides A and B

In Experiment 6, it was revealed that the enzyme of the present invention catalyzes both 2-epimerization and aldose-ketose conversion. Based on the result, it was estimated that Isomerized saccharide A is epilactose which is an epimer of the substrate, lactose, and Isomerized saccharide B is lactulose which is formed from lactose by isomerizing reducing end glucose in lactose into fructose. In the following experiment, the structures of Isomerized saccharides A and B, and commercially available standards of epilactose and lactulose were investigated by nuclear magnetic resonance (NMR) analyses.

The preparations of Isomerized saccharides A and B, obtained in Experiment 7-2, were subjected to $^1$H-NMR analyses conducted by the following conditions. Commercially available standards of epilactose and lactulose were also subjected to the analyses.

Figure 7:
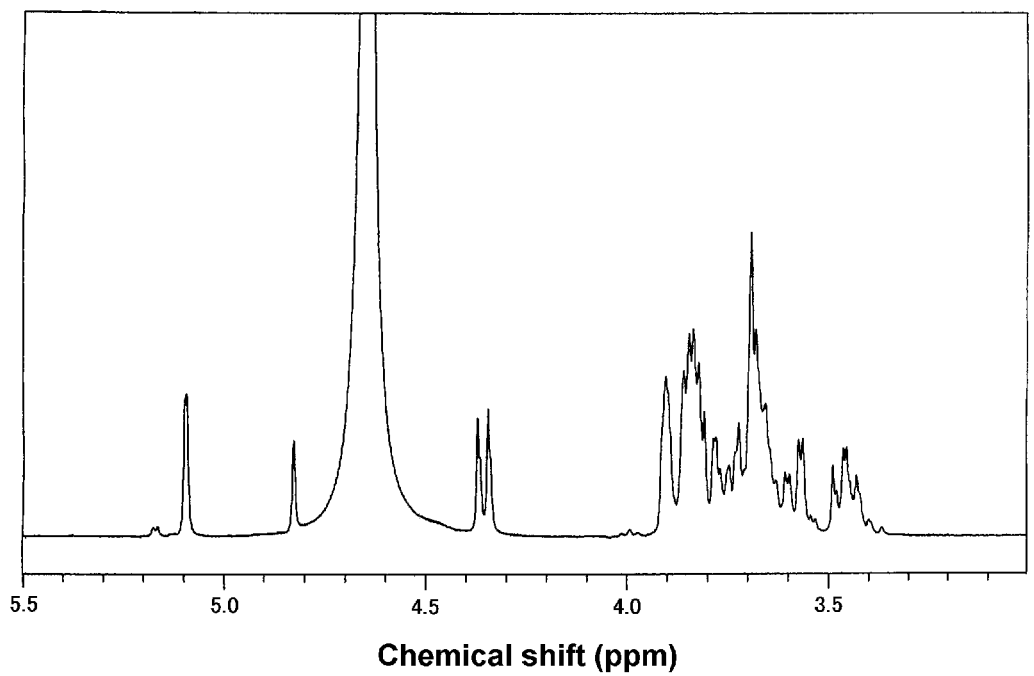
FIG. 7 shows a $^1$H-NMR spectrum of Isomerized Saccharide A isolated from the reaction mixture obtained by allowing the cellobiose 2-epimerase of the present invention to act on lactose.
Figure 8:
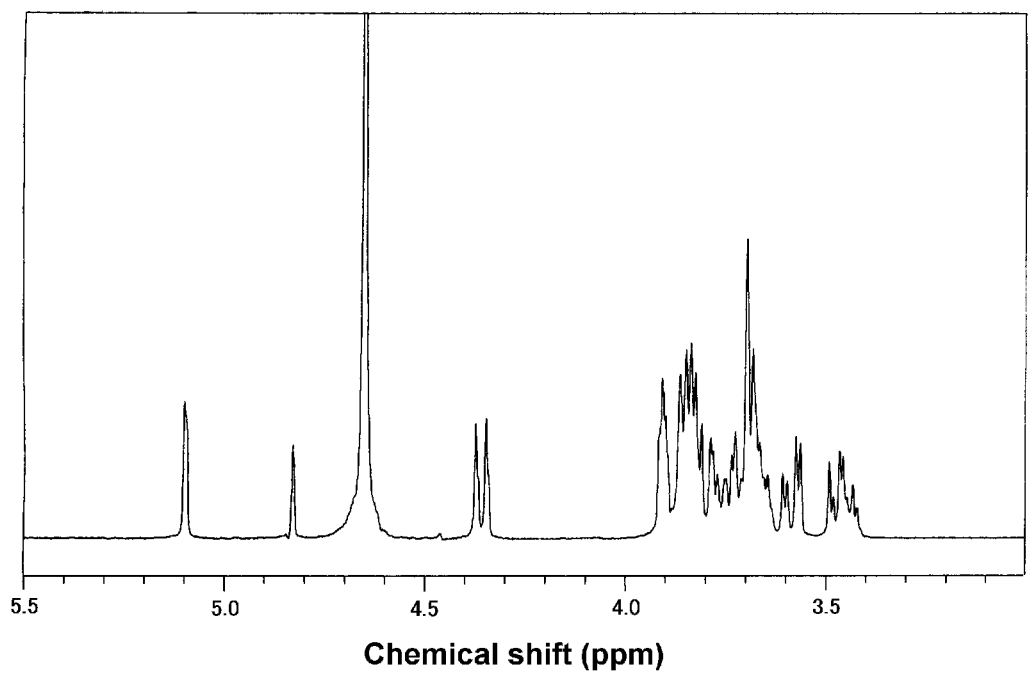
FIG. 8 shows a $^1$H-NMR spectrum of the commercially available epilactose as a standard.
Figure 9:
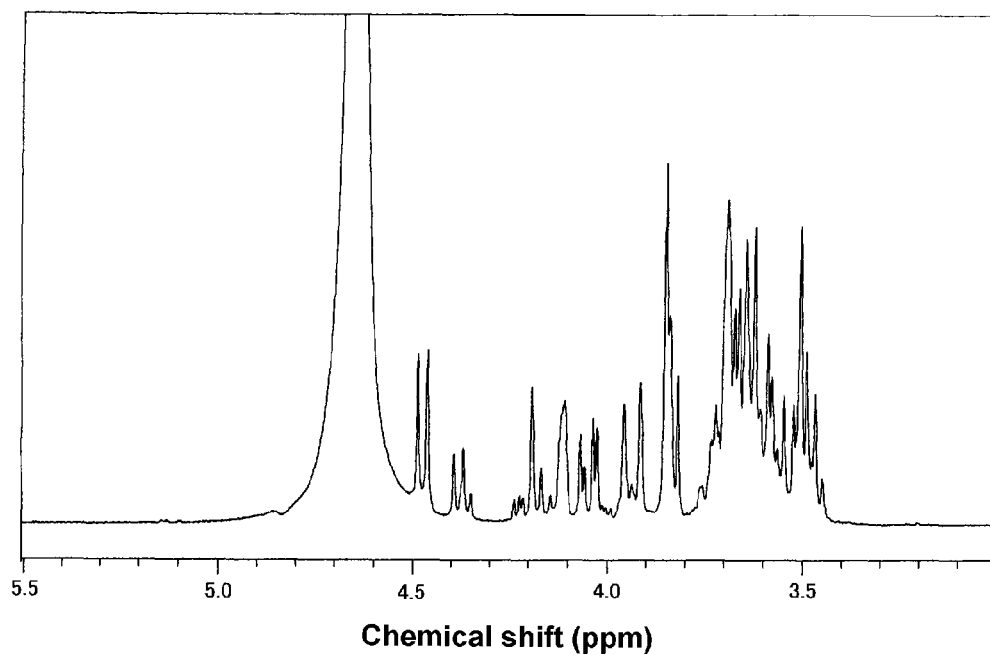
FIG. 9 shows a $^1$H-NMR spectrum of Isomerized Saccharide B isolated from the reaction mixture obtained by allowing the cellobiose 2-epimerase of the present invention to act on lactose.
Figure 10:
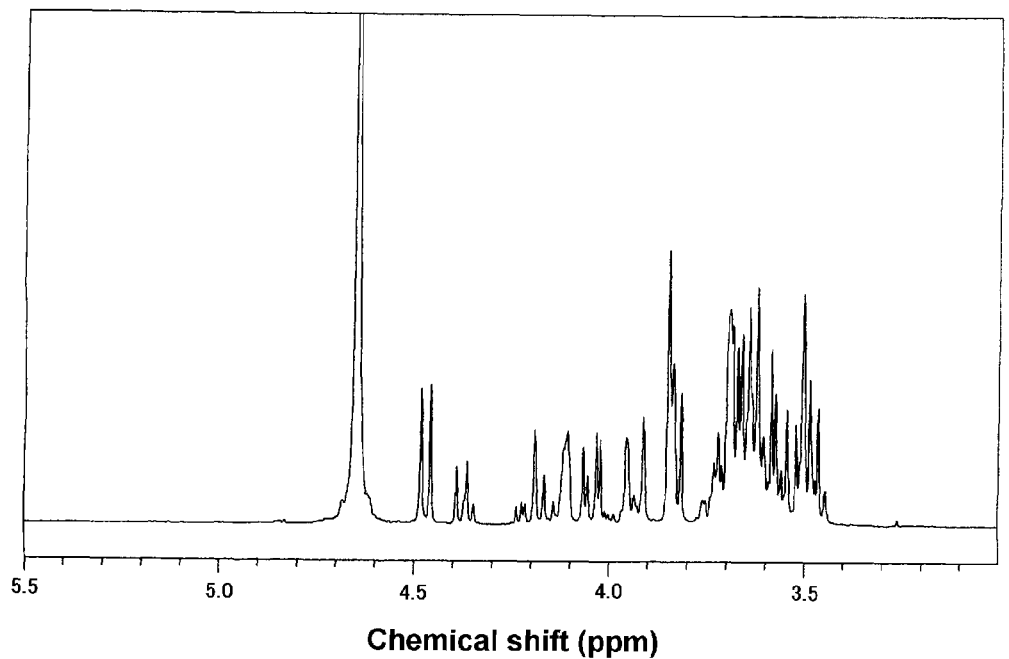
FIG. 10 shows a $^1$H-NMR spectrum of the commercially available lactulose as a standard.

$^1$H-NMR spectra of Isomerized saccharides A and epilactose standard are in FIGS. 7 and 8, respectively. Also, $^1$H-NMR spectra of Isomerized saccharides B and lactuose standard are in FIGS. 9 and 10, respectively.

<Conditions for $^1$H-NMR Analysis>

NMR apparatus: "Model JNM-AL300", produced by JOEL Ltd., Tokyo, Japan

Solvent: D$_2$O

Amount of sample: 20 mg

Magnetic field strength: 300.4 MHz

Integration count: 16

As is evident from FIGS. 7 and 8, $^1$H-NMR spectrum of Isomerized saccharide A was completely identical with that of epilactose standard. As is evident from FIGS. 9 and 10, $^1$H-NMR spectrum of Isomerized saccharide B was completely identical with that of lactulose standard. From the results, it was confirmed that Isomerized saccharides A and B, formed from lactose, are epilactose and lactulose, respectively.

Experiment 8

Isomerized Saccharides Formed from Cellobiose

In order to indentify isomerized saccharides formed from cellobiose by the action of the cellobiose 2-epimerase of the present invention, isomerized saccharides were isolated and subjected to the structural analysis.

Experiment 8-1

Preparation of Isomerized Saccharides from Cellobiose

To a substrate solution prepared by dissolving cellobiose into 20 mM acetate buffer (pH 6.0) to give a concentration of 10% (w/v), 50 units/g-solid substrate of the purified recombinant cellobiose 2-epimerase preparation (10 ml of the enzyme solution) obtained by the method in Experiment 4-4 was added, and followed the enzyme reaction at 60° C. for 23 hours.

Figure 11:
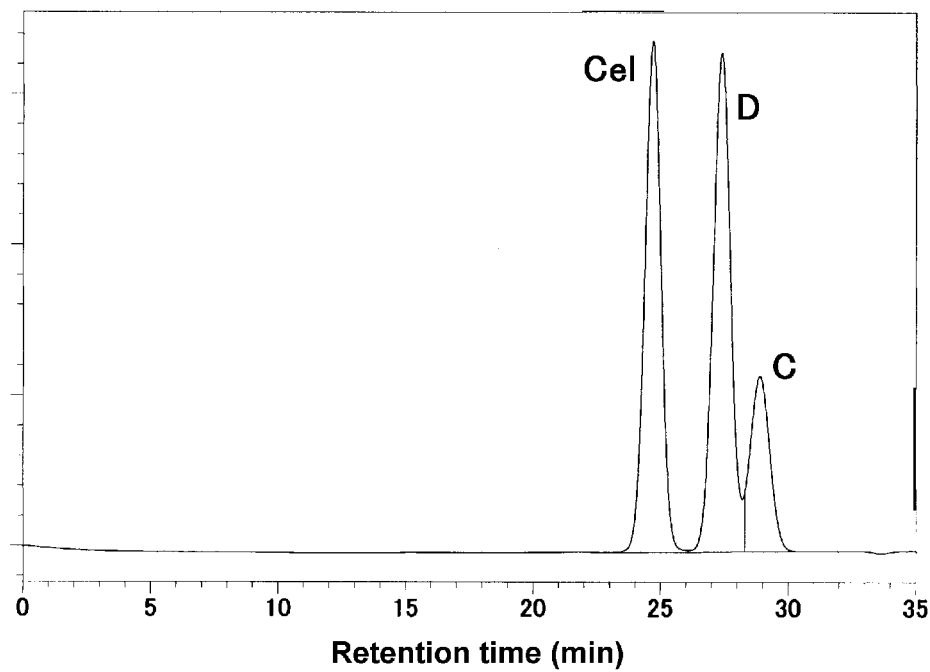
FIG. 11 shows a HPLC chromatogram of the reaction mixture obtained by allowing the cellobiose 2-epimerase of the present invention to act on cellobiose.

After the completion of the reaction, the reaction mixture was heated at 100° C. for 10 minutes to stop the reaction. The saccharide composition of the reaction mixture was determined by the following HPLC analysis. The resulting HPLC chromatogram is shown in FIG. 11.

<Conditions for HPLC Analysis>

Column: "SHODEX SUGAR SP0810", produced by Showa Denko K. K., Tokyo, Japan, and "MCI gel CK08EP", produced by Mitsubishi Chemical Corporation, Tokyo, Japan; The two columns were connected serially in this order;

Eluent: Deionized water

Column temperature: 75° C.

Flow rate: 0.6 ml/min

Detector: "RID-10A", a refractive index detector produced by Shimadzu Corporation, Kyoto, Japan.

As shown in FIG. 11, two peaks deemed to be isomerized saccharides were detected together with a peak of unreacted cellobiose (represented by the symbol, "Cel", in FIG. 11) in the chromatogram of the reaction mixture. In the HPLC analysis, a saccharide eluted at Rt 28.9 min was named as "Isomerized saccharide C" (represented by the symbol, "C", in FIG. 11) and that eluted at Rt 27.4 min was named as "Isomerized saccharide D" (represented by the symbol, "D", in FIG. 11), respectively.

The saccharide composition of the reaction mixture was 40.5% (w/w) of cellobiose, 16.5% (w/w) of Isomerized saccharide C, and 43.0% (w/w) of Isomerized saccharide D.

Experiment 8-2

Isolation and Purification of Isomerized Saccharides C and D

Total 432-mg solid of the reaction mixture obtained in Experiment 8-1 was divided to 100 parts and each part was subjected to HPLC described in Experiment 8-1 for isolating and purifying Isomerized saccharides C and D. Fractions containing Isomerized saccharide C or D were separately collected. Each fraction was concentrated and dried, and 17.9 mg of Isomerized saccharide C with the purity of 100% and 118 mg of Isomerized saccharide D with the purity of 100% were obtained.

Experiment 8-3

Structural Analysis of Isomerized Saccharide C

Experiment 8-3-1

Mass Spectrometry

The preparation of Isomerized saccharide C, obtained in Experiment 8-2, was subjected to mass spectrometry using "LCQ-Advantage", a mass spectrometer produced by Thermo Fisher Scientific Inc., MA, USA. In the mass spectrum, a sodium-attached molecular ion with a molecular mass of 365 was remarkably detected. From the result, it was revealed that the molecular mass of Isomerized saccharide C is 342.

Experiment 8-3-2

Enzymatic Hydrolysis

To 0.3 ml of substrate solution prepared by dissolving Isomerized saccharide C obtained in Experiment 8-2 into 20 mM acetate buffer to give a concentration of 2% (w/v), 500 units/g-substrate of a β-glucosidase preparation commercialized by Oriental Yeast Co., Ltd., Tokyo, Japan, (0.3 ml of the enzyme solution) was added, and followed the enzyme reaction at 40° C. for 16 hours. After stopping the reaction by heating at 100° C. for 10 minutes, the resulting reaction mixture was subjected to the HPLC analysis in Experiment 6 to investigate the reaction products. In the reaction mixture, equimolar D-glucose and D-mannose were detected as monosaccharides. Regarding the result and the substrate specificity of β-glucosidase, it was revealed that Isomerized saccharide C is a disaccharide constructed by binding D-glucose to D-mannose via β-glucosidic linkage.

Experiment 8-3-3

NMR Analysis

According to the conventional method, the preparation of Isomerized saccharide C was subjected to NMR analyses. The $^1$H-NMR spectrum was obtained by the conditions described in Experiment 7-3, and the $^{13}$C-NMR spectrum was obtained by the following conditions.

<Conditions for $^{13}$C-NMR Analysis>

NMR apparatus: "Model JNM-AL300", produced by JOEL Ltd., Tokyo, Japan
Solvent: $D_2O$
Amount of sample: 14 to 30 mg
Magnetic field strength: 75.45 MHz
Integration count: 1,000

Figure 12:
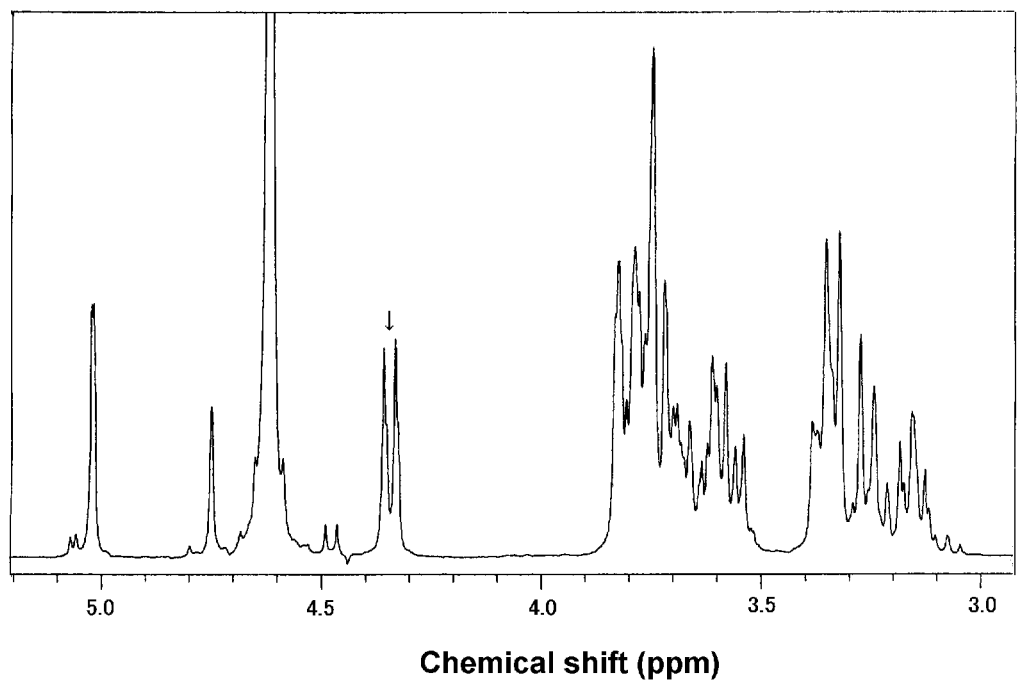
FIG. 12 shows a $^1$H-NMR spectrum of Isomerized Saccharide C isolated from the reaction mixture obtained by allowing the cellobiose 2-epimerase of the present invention to act on cellobiose.
Figure 13:
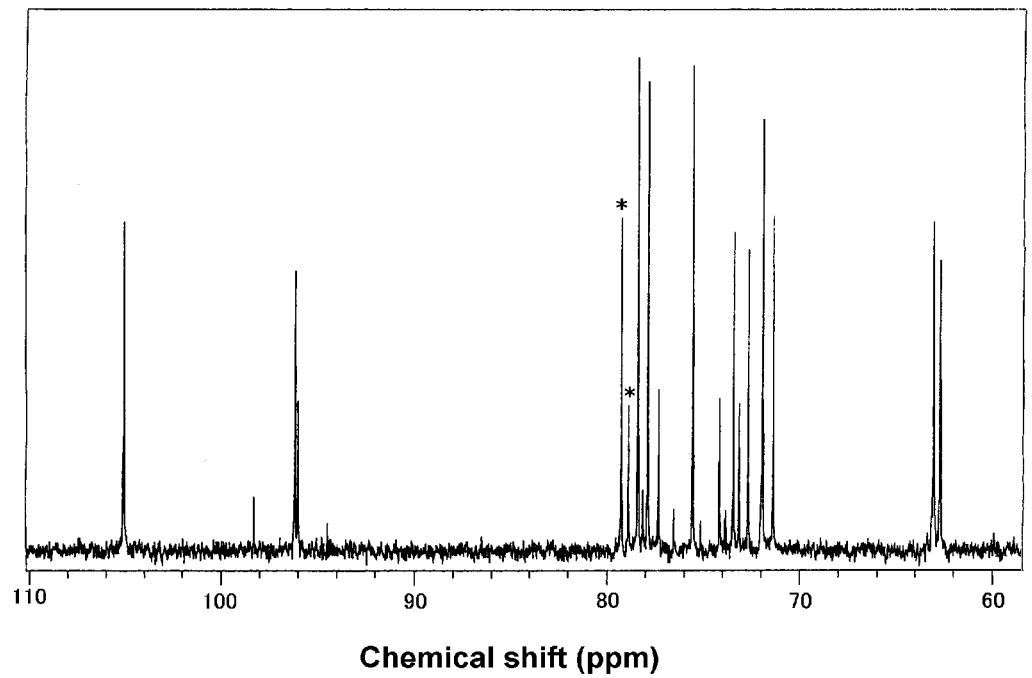
FIG. 13 shows a $^{13}$C-NMR spectrum of Isomerized Saccharide C isolated from the reaction mixture obtained by allowing the cellobiose 2-epimerase of the present invention to act on cellobiose.

The $^1$H-NMR spectrum and $^{13}$C-NMR spectrum of the preparation of Isomerized saccharide C are shown FIGS. 12 and 13, respectively.

In the $^{13}$C-NMR spectrum in FIG. 13, C-4 signals of D-mannose (79.3 and 78.9 ppm, represented by the symbols, "*" in FIG. 13) were shifted to lower direction of magnetic field, revealing that D-glucose binds C-4 hydroxyl group of D-mannose in Isomerized saccharide C. In the $^1$H-NMR spectrum in FIG. 12, a signal at about 4.35 ppm (represented by the symbol, "↓" in FIG. 12) was assigned to C-1 proton of D-glucose residue and the spin-spin coupling constant was about 7.9 Hz, revealing that the anomeric type of C-1 hydroxyl group of D-glucose residue bound to C-4 position of D-mannose is β-type. Further, the chemical sift of each carbon signal in $^{13}$C-NMR spectrum of Isomerized saccharide C was agreed well with that of epicellobiose disclosed in Usui et al., *Agricultural Biological Chemistry*, Vol. 43, pp. 863-865 (1979).

From the results in Experiments 8-3-1 and 8-3-3, it was revealed that Isomerized saccharide C, formed from cellobiose by the action of the epimerase of the present invention, is 4-O-b-D-glucosyl-D-mannose, i.e., epicellobiose.

Experiment 8-4

Structural Analysis of Isomerized Saccharide D

Experiment 8-4-1

Mass Spectrometry

Isomerized saccharide D, obtained in Experiment 8-2, was subjected to mass spectrometry similarly with the case of Experiment 8-3-1. In the mass spectrum, a sodium-attached molecular ion with a molecular mass of 365 was remarkably detected. From the result, it was revealed that the molecular mass of Isomerized saccharide C is 342.

Experiment 8-4-2

Enzymatic Hydrolysis

Except for using Isomerized saccharide D obtained in Experiment 8-2 as a substitute of Isomerized saccharide C, enzymatic hydrolysis analysis was carried out by the same method in Experiment 8-3-2. The resulting reaction mixture was subjected to the HPLC analysis in Experiment 6 to investigate the reaction products. In the reaction mixture, equimolar D-glucose and D-fructose were detected as monosaccharides. Regarding the result and the substrate specificity of β-glucosidase, it was revealed that Isomerized saccharide D is a disaccharide constructed by binding D-glucose to D-fructose via β-glucosidic linkage.

Experiment 8-4-3

NMR-Analysis

Similarly with the case of Experiment 8-3-3, the preparation of Isomerized saccharide D, obtained in Experiment 8-2 was subjected to NMR-analyses. The $^1$H-NMR spectrum and $^{13}$C-NMR spectrum of Isomerized saccharide D are shown FIGS. 14 and 15, respectively. In the $^{13}$C-NMR spectrum in FIG. 15, C-4 signals of D-fructose (79.9, 86.4 and 87.7 ppm, represented by the symbols, "*" in FIG. 15) were shifted to lower direction of magnetic field, revealing that D-glucose binds C-4 hydroxyl group of D-fructose in Isomerized saccharide D. In the $^1$H-NMR spectrum in FIG. 14, signals at about 4.49, 4.40, and 4.38 ppm (represented by the symbols, "↓" in FIG. 14) were assigned to C-1 proton of D-glucose residue and the spin-spin coupling constants were about 7.9 Hz (a signal at about 4.49 ppm), about 7.7 Hz (a signal at about 4.40 ppm), and about 6.1 Hz (a signal at about 4.38 ppm), revealing that the anomeric type of C-1 hydroxyl group of D-glucose residue bound to C-4 position of D-fructose is β-type. Further, the chemical sift of each carbon signal in $^{13}$C-NMR spectrum of Isomerized saccharide D was agreed well with that of cellobiulose disclosed in Pfeffer et al., *Carbohydrate Research*, Vol. 102, pp. 11-22 (1982).

From the results in Experiments 8-4-1 and 8-4-3, it was revealed that Isomerized saccharide D, formed from cellobiose by the action of the epimerase of the present invention, is 4-O-β-D-glucosyl-D-fructose, i.e., cellobiulose.

Experiment 9

Isomerized Saccharides Formed from Maltose

In order to indentify isomerized saccharides formed from maltose by the action of the cellobiose 2-epimerase of the present invention, isomerized saccharides were isolated and subjected to the structural analysis.

Experiment 9-1

Preparation of Isomerized Saccharides from Maltose

Figure 16:
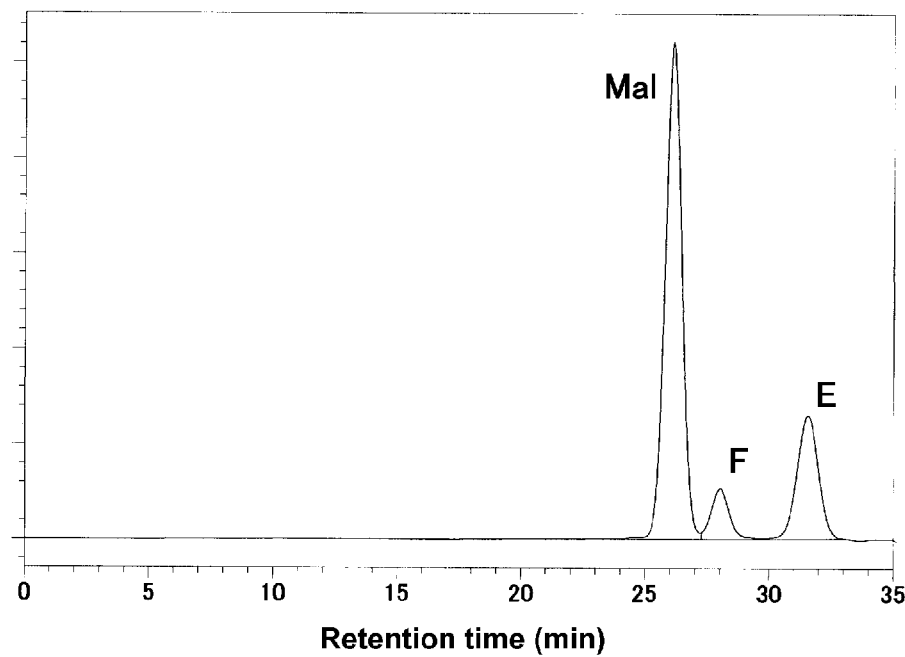
FIG. 16 shows a HPLC chromatogram of the reaction mixture obtained by allowing the cellobiose 2-epimerase of the present invention to act on maltose.

Except for using maltose as a substitute of cellobiose and using 200 units/g-solid substrate of the recombinant cellobiose 2-epimerase, obtained by the method in Experiment 4-4, an enzyme reaction was carried out by the same method in Experiment 8-1 and the reaction mixture was obtained. The HPLC chromatogram of the reaction mixture is shown in FIG. 16. As shown in FIG. 16, two peaks deemed to be isomerized saccharides were detected together with a peak (represented by the symbol, "Mal", in FIG. 16) of unreacted maltose. In the HPLC chromatogram, a saccharide eluted at 31.6 min (represented by the symbol, "E", in FIG. 16) was named as "Isomerized saccharide E", and another saccharide eluted at 28.0 min (represented by the symbol, "F", in FIG. 16) was named as "Isomerized saccharide F". The saccharide composition of the reaction mixture was 70.1% (w/w) of maltose, 22.2% (w/w) of Isomerized saccharide E, and 7.7% (w/w) of Isomerized saccharide F.

Experiment 9-2

Isolation and Purification of Isomerized Saccharides E and F

Total 191 mg-solid of the reaction mixture obtained in Experiment 9-1 was divided to 29 parts and each part was subjected to HPLC described in Experiment 8-1 for isolating and purifying Isomerized saccharides E and F. Each Fraction containing Isomerized saccharide E or F was concentrated and dried, and 38.1 mg of Isomerized saccharide E with the purity of 99.1% and 14.2 mg of Isomerized saccharide F with the purity of 92.3% were obtained.

Experiment 9-3

Structural Analysis of Isomerized Saccharide E

Experiment 9-3-1

Mass Spectrometry

Isomerized saccharide E, obtained in Experiment 9-2, was subjected to mass spectrometry similarly with the case of Experiment 8-3-1. In the mass spectrum, a sodium-attached molecular ion with a molecular mass of 365 was remarkably detected. From the result, it was revealed that the molecular mass of Isomerized saccharide E is 342.

Experiment 9-3-2

Enzymatic Hydrolysis

To 0.3 ml of substrate solution prepared by dissolving Isomerized saccharide E obtained in Experiment 9-2 into 20 mM acetate buffer to give a concentration of 2% (w/v), 500 units/g-substrate of a α-glucosidase preparation commercialized by Oriental Amano Enzyme Inc., Aichi, Japan, (0.3 ml of the enzyme solution) was added, and followed the enzyme reaction at 50° C. for 16 hours. After stopping the reaction by heating at 100° C. for 10 minutes, the resulting reaction mixture was subjected to the HPLC analysis described in Experiment 6 to investigate the reaction products. In the reaction mixture, equimolar D-glucose and D-mannose were detected as monosaccharides. Regarding the result and the substrate specificity of α-glucosidase, it was revealed that Isomerized saccharide E is a disaccharide constructed by binding D-glucose to D-mannose via α-glucosidic linkage.

Experiment 9-3-3

NMR-Analysis

Similarly with the case of Experiment 8-3-3, the preparation of Isomerized saccharide E, obtained in Experiment 9-2 was subjected to NMR-analyses. The $^1$H-NMR spectrum and $^{13}$C-NMR spectrum of Isomerized saccharide E are shown FIGS. 17 and 18, respectively. In the $^{13}$C-NMR spectrum in FIG. 18, C-4 signals of D-mannose (77.7 and 77.2 ppm, represented by the symbols, "*" in FIG. 18) were shifted to lower direction of magnetic field, revealing that D-glucose binds C-4 hydroxyl group of D-mannose in Isomerized saccharide E. In the $^1$H-NMR spectrum in FIG. 17, a signal at about 5.22 ppm (represented by the symbol, "↓" in FIG. 17) was assigned to C-1 proton of D-glucose residue and the spin-spin coupling constant was about 3.9 Hz, revealing that the anomeric type of C-1 hydroxyl group of D-glucose residue bound to C-4 position of D-mannose is α-type.

Further, the chemical sift of each carbon signal in $^{13}$C-NMR spectrum of Isomerized saccharide E was agreed well with that of 4-O-α-D-glucosyl-D-mannose disclosed in Japanese Patent Kokai No. 95,794/98.

From the results in Experiments 9-3-1 and 9-3-3, it was revealed that Isomerized saccharide E, formed from maltose by the action of the epimerase of the present invention, is 4-O-α-D-glucosyl-D-mannose, i.e., epimaltose.

Experiment 9-4

Structural Analysis of Isomerized Saccharide F

In Experiment 6, it was reveled that the enzyme of the present invention catalyzes aldose-ketose conversion in addition to 2-epimerization and formed lactulose from lactose in Experiment 7, and formed cellobiuose from cellobiose in Experiment 8. Accordingly, it was considered that Isomerized saccharide F is maltulose formed by the isomerization of reducing end glucose of maltose into fructose. In the following experiment, Isomerized saccharide F and commercially available maltulose standard were subjected to $^1$H-NMR analysis.

$^1$H-NMR analysis was carried out using the preparation of Isomerized saccharide F, obtained in Experiment 9-2, by the same conditions in Experiment 7-3. The commercially available maltulose standard was also subjected to the analysis.

Figure 19:
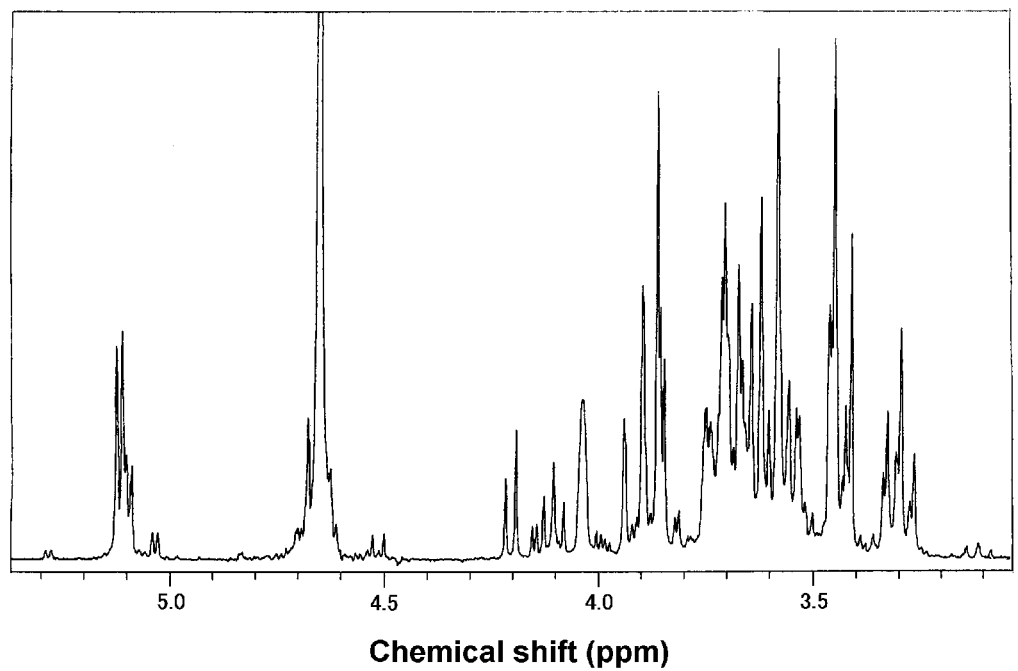
FIG. 19 shows a $^1$H-NMR spectrum of Isomerized Saccharide F isolated from the reaction mixture obtained by allowing the cellobiose 2-epimerase of the present invention to act on maltose.
Figure 20:
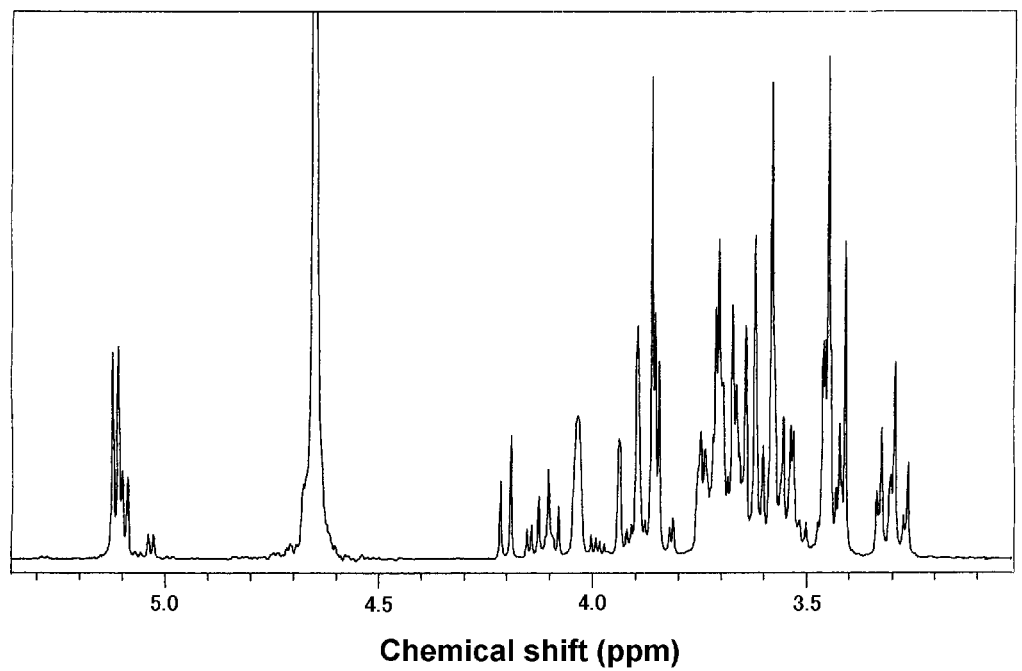
FIG. 20 shows a $^1$H-NMR spectrum of the commercially available maltulose as a standard.

The $^1$H-NMR spectra of Isomerized saccharide F and maltulose standard are in FIGS. 19 and 20, respectively.

As is evident from FIGS. 19 and 20, the $^1$H-NMR spectrum of Isomerized saccharide F was completely identical with that of maltulose standard. From the results, Isomerized saccharide F formed from maltose was identified as maltulose.

Experiment 10

Isomerized Saccharide Formed from Maltotriose

In order to indentify an isomerized saccharide formed from maltotriose by the action of the cellobiose 2-epimerase of the present invention, isomerized saccharides were isolated and subjected to the structural analysis.

Experiment 10-1

Preparation of an Isomerized Saccharide from Maltotriose

Figure 21:
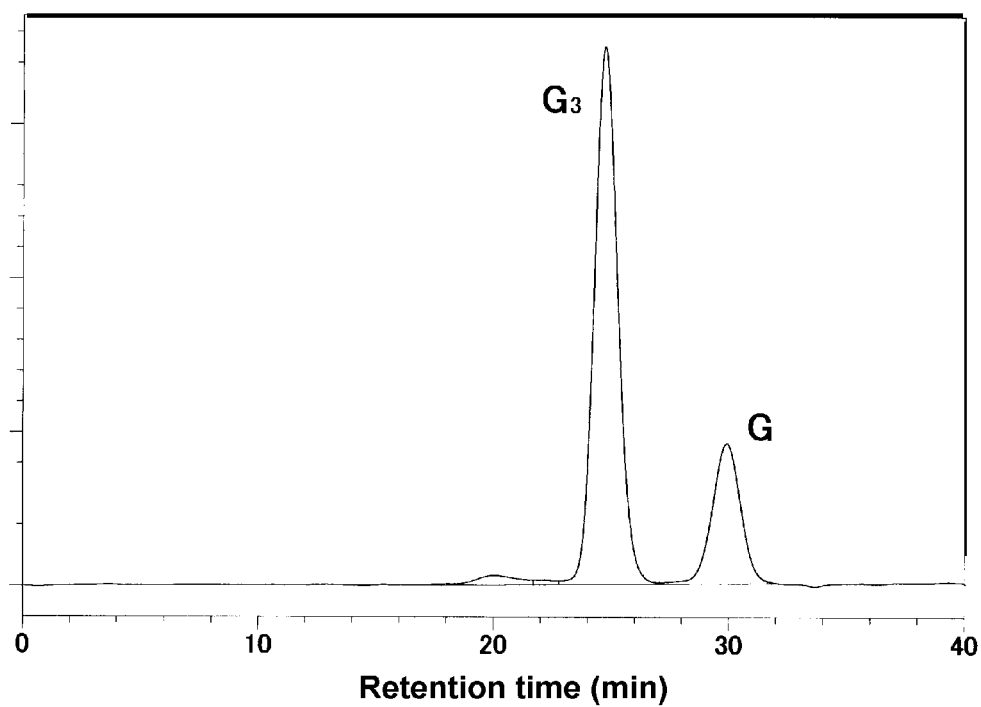
FIG. 21 shows a HPLC chromatogram of the reaction mixture obtained by allowing the cellobiose 2-epimerase of the present invention to act on maltotriose.

Except for using maltotriose as a substitute of maltose, an enzyme reaction was carried out by the same method in Experiment 9-1 and the reaction mixture was obtained. The HPLC chromatogram of the reaction mixture is shown in FIG. 21. As shown in FIG. 21, one peak deemed to be isomerized saccharide were detected together with a peak (represented by the symbol, "G$_3$", in FIG. 21) of unreacted maltotriose. In the HPLC chromatogram, a saccharide eluted at 29.9 min (represented by the symbol, "G", in FIG. 21) was named as "Isomerized saccharide G". The saccharide composition of the reaction mixture was 73.8% (w/w) of maltotriose, 23.3% (w/w) of Isomerized saccharide G, and 2.9% (w/w) of unknown saccharide.

Experiment 10-2

Isolation and Purification of Isomerized Saccharide G

Total 475 mg-solid of the reaction mixture obtained in Experiment 10-1 was divided into 80 parts and each part was subjected to HPLC described in Experiment 8-1 for isolating and purifying Isomerized saccharide G. Fractions containing Isomerized saccharide G were concentrated and dried, and 113 mg of Isomerized saccharide G with the purity of 99.4% was obtained.

Experiment 10-3

Structural Analysis of Isomerized Saccharide G

Experiment 10-3-1

Mass Spectrometry

Isomerized saccharide G, obtained in Experiment 10-2, was subjected to mass spectrometry similarly with the case of Experiment 8-3-1. In the mass spectrum, a sodium-attached molecular ion with a molecular mass of 527 was remarkably detected.

From the result, it was revealed that the molecular mass of Isomerized saccharide G is 504.

Experiment 10-3-2

Enzymatic Hydrolysis

Except for using Isomerized saccharide G obtained in Experiment 10-2 as a substitute of Isomerized saccharide E, enzymatic hydrolysis using α-glucosidase was carried out by the same method in Experiment 9-3-2. The resulting reaction mixture was subjected to the HPLC analysis to investigate the reaction products. In the reaction mixture, D-glucose and D-mannose were detected as monosaccharides in a molar ratio of 2:1. Regarding the result and the substrate specificity of α-glucosidase, it was revealed that Isomerized saccharide G is a trisaccharide constructed by one D-mannose molecule at the reducing end and two D-glucose molecules.

Experiment 10-3-3

NMR-Analysis

Similarly with the case of Experiment 8-3-3, the preparation of Isomerized saccharide G, obtained in Experiment 10-2 was subjected to NMR-analyses. The $^1$H-NMR spectrum and $^{13}$C-NMR spectrum of Isomerized saccharide G are shown FIGS. 22 and 23, respectively. In the $^{13}$C-NMR spectrum in FIG. 23, C-4 signals of D-mannose (77.9 and 77.3 ppm, represented by the symbols, "*" in FIG. 23) were shifted to lower direction of magnetic field, revealing that D-glucose binds C-4 hydroxyl group of D-mannose in Isomerized saccharide G. Also, a C-4 signal of one D-glucose molecule (79.2 ppm, represented by the symbol, "#" in FIG. 23) was shifted to lower direction of magnetic field, revealing that one D-glucose molecule binds C-4 hydroxyl group of D-glucose in Isomerized saccharide G. Further, in the $^1$H-NMR spectrum in FIG. 22, a signal at about 5.20 ppm (represented by the symbol, "↓" in FIG. 22) was assigned to C-1 proton of D-glucose residue bound to D-mannose and the spin-spin coupling constant was about 3.9 Hz, revealing that the anomeric type of C-1 hydroxyl group of D-glucose residue bound to C-4 position of D-mannose is α-type. Furthermore, a signal at about 5.26 ppm (represented by the symbol "x" in FIG. 22) was assigned to C-1 proton of D-glucose residue bound to D-glucose and the spin-spin coupling constant was about 3.7 Hz, revealing that the anomeric type of C-1 hydroxyl group of D-glucose residue bound to C-4 position of D-glucose is also α-type.

From the results in Experiments 10-3-1 to 10-3-3, it was revealed that Isomerized saccharide G, formed from maltotriose by the action of the epimerase of the present invention, is 4-O-α-D-glucosyl-4-O-α-glucosyl-D-mannose, i.e., epimaltotriose.

Experiment 11

Formation of Isomerized Saccharides from Various Saccharides

—Effect of the Amount of Enzyme—

From the results in Experiments 5 to 10, it was revealed that the cellobiose 2-epimerase of the present invention acts on monosaccharides such as D-glucose, D-galactose, D-fructose, D-mannose, D-tagatose, etc.; disaccharides such as maltose, cellobiose, lactose, etc.; and oligosaccharides such as maltooligosachaide, cellooligosaccharide, etc.; and catalyzes 2-epimeization and aldose-ketose conversion. In this experiment, the effects of the amount of enzyme on the isomerization of various substrates were investigated.

Six kinds of monosaccharide, i.e., D-glucose, D-galactose, D-mannose, D-talose, D-fructose, and D-tagatose; 3 kinds of disaccharide, i.e., maltose, cellobiose, and lactose; and 1 kind of trisaccharide, maltotriose; were used as substrates.

Each of them was dissolved into 20 mM acetate buffer (pH 6.0), admixed with the purified preparation of the recombinant cellobiose 2-epimerase, obtained by the method in Experiment 4-4, and followed the enzyme reaction under the conditions of 10% (w/v) substrate concentration, 60° C. for 72 hours. The amount of enzyme was set to 130 or 500 units/g-substrate when monosaccharide was used as the substrate, and to 1 or 130 units/g-substrate when disaccharide or trisaccharide was used as the substrate. Each reaction mixture was heated at 100° C. for 10 minutes to stop the reaction and subjected to HPLC analysis to determine the contents of isomerized saccharide, on a dry solid basis. The contents of epilactose and lactulose in the reaction mixture obtained using lactose as substrate were determined by GC analysis described in Experiment 1-2. The results are in Table 5.

TABLE 5

| Substrate | | Formed isomerized saccharide | Content of isomerized saccharide in the reaction mixture (%) Amount of enzyme (Units/g-substrate) | | |
|---|---|---|---|---|---|
| | | | 1 | 130 | 500 |
| Monosaccharide | D-Glucose | D-Mannose | —* | 20.9 | 23.3 |
| | | D-Fructose | | 5.0 | 9.2 |
| | D-Galactose | D-Talose | —* | —* | 11.0 |
| | | D-Tagatose | | | 9.2 |
| | D-Mannose | D-Glucose | —* | 45.8 | —* |
| | | D-Fructose | | 6.6 | |
| | D-Talose | D-Galactose | —* | —* | 27.2 |
| | | D-Tagatose | | | 17.9 |
| | D-Fructose | D-Glucose | —* | 2.2 | —* |
| | | D-Mannose | | 2.2 | |
| | D-Tagatose | D-Galactose | —* | —* | 4.7 |
| | | D-Talose | | | 5.2 |
| Disaccharide | Maltose | Epimaltose | —* | 22.2 | —* |
| | | Maltulose | | 7.7 | |
| | Cellobiose | Epicellobiose | 27.8 | 13.4 | —* |
| | | Cellobiulose | 1.7 | 53.2 | |
| | Lactose | Epilactose | 32.0 | 12.8 | —* |
| | | Lactulose | 0.0 | 57.5 | |
| Trisaccharide | Maltotriose | Epimaltotriose | —* | 23.3 | —* |

*Not tested.

As is evident from Table 5, the cellobiose 2-epimerase of the present invention relatively specifically acted on cellobiose and lactose and formed epicellobiose and epilactose by catalyzing 2-epimerization even in the case of using relatively low amount of enzyme, 1 unit/g-substrate. In the case of increasing the amount of enzyme, the enzyme catalyzed aldose-ketose conversion and remarkably formed cellobiulose and lactulose. The action of the enzyme on monosaccharide and trisaccharide was relatively weak in comparison with the cases of cellobiose and lactose, and a large amount of enzyme was required for the isomerization of them.

The physicochemical properties and substrate specificities of the cellobiose 2-epimerase from *Caldicellulosiruptor saccharolyticus* ATCC43494, obtained from above experiments, were shown in Table 6 together with those of conventional cellobiose 2-epimerases from *Ruminococcus albus* (excerpted from Non-Patent Document 3) and *Eubacterium cellosolvens* (excerpted from Non-Patent Document 4).

TABLE 6

| Physicochemical property | *Caldicellulosiruptor saccharolyticus* ATCC43494 | *Ruminococcus albus* NE1 | *Eubacterium cellosolvens* NE13 |
|---|---|---|---|
| Molecular weight (Dalton)* | 44,000 ± 5,000 | 43,100 | 46,700 |
| Optimum temperature | 80° C. | 30° C. | 35° C. |
| Optimum pH | 7.8 | 7.5 | 7.0-8.5 |
| Thermal stability | up to 70° C. | —** | up to 40° C. |
| pH stability | 4.5-9.5 | —** | 4.0-8.0 |
| Inhibition by metal ions | $Al^{3+}$, $Fe^{2+}$, $Fe^{3+}$, $Pb^{2+}$, $Cu^{2+}$, $Zn^{2+}$, $Hg^{2+}$ | $Al^{3+}$, $Fe^{3+}$, $Co^{2+}$, $Pb^{2+}$, $Cu^{2+}$, $Zn^{2+}$, $Ag^{2+}$ | —** |
| Substrate specificity D-Glucose | Forming D-mannose and D-fructose | Not acted | Not acted |
| D-Mannose | Forming D-glucose and D-fructose | Not acted | Not acted |
| D-Galactose | Forming D-talose and D-tagatose | —** | Not acted |
| Maltose | Forming epimaltose and maltulose | Not acted | —** |
| Cellobiose | Forming epicellobiose and cellobiulose | Forming epicellobiose | Forming epicellobiose |
| Lactose | Forming epilactose and lactulose | Forming epilactose | Forming epilactose |

*SDS-polyacrylamide gel electrophoresis
**Not described

As is evident from Table 6, the cellobiose 2-epimerase from *Caldicellulosiruptor saccharolyticus* ATCC43494 was a thermostable enzyme showing 45 to 50° C. higher optimum temperature and about 30° C. higher thermostability than conventional cellobiose 2-epimerases from *Ruminococcus albus* and *Eubacterium cellosolvens*. Further, it was revealed that the cellobiose 2-epimerase from *Caldicellulosiruptor saccharolyticus* ATCC43494 is a novel enzyme which acts on monosaccharides such as D-glucose, D-galactose and D-mannose, and maltose, while it has been reported that conventional cellobiose 2-epimerases from *Ruminococcus albus* and *Eubacterium cellosolvens* does not act on those saccharides (See Non-patent document 3 and 4).

The followings explain the present invention in detail. However, the present invention is not restricted by them.

Example 1

Preparation of D-Mannose

To 10% (w/v) aqueous D-glucose solution (pH 6.5), 130 units/g-D-glucose, as lactose 2-epimerase activity, of a recombinant cellobiose 2-epimerase purified by the method in Experiment 4-4 was added and allowed to react at 60° C.

for 48 hours. As a result, 21% (w/w) of D-mannose was formed in the reaction mixture. After the reaction, according to the conventional methods, the reaction mixture was decolored by using activated charcoal, deionized by using "DIAION SK1B" (H$^+$-form), a cation exchange resin commercialized by Mitsubishi Chemical Corporation, Tokyo, Japan, and "DIAION WA30" (OH$^-$-form), an anion exchange resin commercialized by Mitsubishi Chemical Corporation, Tokyo, Japan, and concentrated under reduced pressure to make into a syrup containing D-mannose. Then, the syrup was subjected to column chromatography using "DIAION UBK-530" (Ca$^{2+}$-form), a strong acid cation exchanger resin commercialized by Mitsubishi Chemical Corporation, Tokyo, Japan, for isolating and purifying D-mannose and concentrated, and D-mannose in a syrupy form was obtained in a yield of about 18%, on a dry solid basis.

Example 2

Preparation of Epilactose

To 10% (w/v) aqueous lactose solution (pH 6.5), 2 units/g-lactose, as lactose 2-epimerase activity, of a recombinant cellobiose 2-epimerase purified by the method in Experiment 4-4 was added and allowed to react at 60° C. for 72 hours. The reaction mixture was heated at 100° C. for 15 minutes to stop the reaction, cooled and subjected to HPLC and GC analyses for measuring the saccharide composition. It was revealed that the reaction mixture contained 69% (w/w) of unreacted lactose, 28% (w/w) of epilactose, and 3% (w/w) of lactulose.

After adjusting the reaction mixture to pH 4.5, the reaction mixture was admixed with 25 units/g-substrate of "LACTASE Y-AO", a lactase preparation commercialized by Yakult Pharmaceutical Industry Co., Ltd., Tokyo, Japan, and followed the enzyme reaction at 40° C. for 16 hours to preferentially hydrolyze lactose and lactulose in the mixture. After the reaction, the resulting reaction mixture was decolored, deionized and concentrated to obtain a clear syrup containing epilactose. The syrup was subjected to the column chromatography using the strong acid cation exchange resin by the same method in Example 1 for isolating and purifying epilactose. The resulting epilactose fraction was concentrated, and epilactose in a syrupy form was obtained in a yield of about 23%, on a dry solid basis.

Example 3

Preparation of a Syrup Containing Epicellobiose

To 10% (w/v) aqueous cellobiose solution (pH 6.5), 2 units/g-cellobiose, as lactose 2-epimerase activity, of a recombinant cellobiose 2-epimerase purified by the method in Experiment 4-4 was added and allowed to react at 60° C. for 72 hours. The reaction mixture was heated at 100° C. for 10 minutes to stop the reaction, cooled and subjected to HPLC and GC analyses to measure the saccharide composition. By the analyses, it was revealed that the reaction mixture contains 69% (w/w) of unreacted cellobiose, 28% (w/w) of epicelobiose, and 3% (w/w) of cellobiulose, on a dry solid basis. The reaction mixture was decolored, deionized and concentrated by the same methods in Example 1, and a clear syrup containing epicellobiose was obtained in a yield of about 97%, on a dry solid basis.

Example 4

Preparation of a Syrup Containing Epimaltose

To 10% (w/v) aqueous maltose solution (pH 7.3), 200 units/g-maltose, as lactose 2-epimerase activity, of a recombinant cellobiose 2-epimerase purified by the method in Experiment 4-4 was added and allowed to react at 60° C. for 23 hours. The reaction mixture was heated at 100° C. for 10 minutes to stop the reaction, cooled and subjected to HPLC analysis to measure the saccharide composition. By the analysis, it was revealed that the reaction mixture contained 70% (w/w) of unreacted maltose, 22% (w/w) of epimaltose, and 8% (w/w) of maltulose, on a dry solid basis. The reaction mixture was decolored, deionized and concentrated by the same methods in Example 1, and a clear syrup containing epimaltose was obtained in a yield of about 96%, on a dry solid basis.

Example 5

Preparation of Cellobiulose

Except for using 130 units/g-cellobuiose, as lactose 2-epimerase activity, of a recombinant cellobiose 2-epimerase purified by the method in Experiment 4-4, the enzyme was allowed to act on cellobiose by the same method in Example 3. After the reaction, the saccharide composition of the reaction mixture was analyzed by HPLC. It was revealed that the reaction mixture contained 33% (w/w) of unreacted cellobiose, 13% (w/w) of epicellobiose, and 54% (w/w) of cellobiulose. The reaction mixture was decolored, deionized and concentrated to obtain a clear syrup by the same method in Example 3. Successively, the syrup was subjected to the column chromatography using the strong acid cation exchange resin by the same method in Example 1 for isolating and purifying cellobiulose. The resulting cellobiulose fraction was concentrated, and cellobiulose in a syrupy form was obtained in a yield of about 45%, on a dry solid basis.

Example 6

Immobilized Cellobiose 2-Epimerase

A transformant, "ETCS1", was cultured by the method in Experiment 4-4 and 100 g-wet weight of cells expressing cellobiose 2-epimerase activity was obtained by centrifuging the culture broth. Successively, the wet cells were admixed with 100 ml of 2.5% sodium alginate solution prepared by dissolving sodium alginate, commercialized by Wako Pure Chemical Industries, Osaka, Japan, into 20 mM Tris-HCl buffer (pH 7.5). The resulting slurry containing cells was continuously dropped into 0.1 M CaCl$_2$ aqueous solution stirring using a magnetic stirrer from the height of about 20 cm to the surface of the solution to make into spherical gels with a diameter of about 2 mm. After keeping the resulting gels in 0.1 M CaCl$_2$ aqueous solution for about 2 hours, the solution was filtrated by aspiration and alginate-immobilized cells were collected. Since the immobilized cells express cellobiose 2-epimerase, it can be advantageously used as an immobilized cellobiose 2-epimerase by packing in a column.

INDUSTRIAL APPLICABILITY

Since the cellobiose 2-epimerase of the present invention has advantageous thermal stability in comparison with conventional cellobiose 2-epimerases and catalyzes novel saccharide-isomerizing reactions, the enzyme is a significantly useful enzyme for producing saccharides of high value in an industrial scale from materials in a low cost. For example, the enzyme can be used for producing D-mannose from D-glucose; epimaltose from maltose; epicellobiose and cellobiulose from cellobiose; and epilactose and lactulose from lactose. The present invention, having these outstanding functions and effects, is a significantly important invention that greatly contributes to this art.

The invention claimed is:

1. A process for producing an isomerized saccharide selected from the group consisting of D-mannose, D-talose, epimaltose, and epimaltooligosaccharide with a glucose polymerization degree of 3 or higher, comprising the steps of:
  (1) allowing a cellobiose 2-epimerase to act on a material saccharide selected from the group consisting of D-glucose, D-galactose, maltose, and maltooligosaccharide with a glucose polymerization degree of 3 or higher, at a temperature of 55° C. or more, for forming a corresponding isomerized saccharide selected from the group consisting of D-mannose, D-talose, epimaltose, and epimaltooligosaccharide with a glucose polymerization degree of 3 or higher;
  wherein said cellobiose 2-epimerase catalyzes the following isomerizations:
  (a) 2-Epimerization
    epimerizing the 2-hydroxyl group of D-glucose and D-galactose to convert D-glucose and D-galactose into corresponding D-mannose and D-talose, and vice versa;
    epimerizing the 2-hydroxyl group of the reducing end glucose in maltose, cellobiose, and lactose to convert maltose, cellobiose, and lactose into corresponding epimaltose, epicellobiose, and epilactose; and
    epimerizing the 2-hydroxyl group of the reducing end glucose in a maltooligosaccharide and cellooligosaccharide, which have a glucose polymerization degree of 3 or higher, to convert the maltooligosaccharide and cellooligosaccharide into corresponding epimaltooligosaccharide and epicellooligosaccharide; and
  (b) Aldose-Ketose conversion
    converting D-glucose or D-mannose into D-fructose, and vice versa;
    converting D-galactose or D-talose into D-tagatose, and vice versa;
    converting maltose or epimaltose into maltulose;
    converting cellobiose or epicellobiose into cellobiulose; and
    converting lactose or epilactose into lactulose; and
  (2) decolorizing, deionizing, and concentrating the isomerized saccharide formed in step (1),
  wherein said cellobiose 2-epimerase is selected from the group consisting of a cellobiose 2-epimerase having the amino acid sequence of SEQ ID NO:10 and a recombinant cellobiose 2-epimerase having a variant amino acid sequence of SEQ ID NO:10, where one or more but less than 10 amino acid residues in SEQ ID NO:10 are replaced, deleted, or added without altering the enzyme activities in (a) and (b).

2. A process for producing isomerized saccharide selected from the group consisting of D-fructose, D-tagatose, maltulose, cellobiulose, and lactulose, comprising the steps of:
  (1) allowing a cellobiose 2-epimerase to act on a material saccharide selected from the group consisting of D-glucose, D-galactose, maltose, cellobiose, and lactose, at a temperature of 55° C. or more for forming a corresponding isomerized saccharide selected from the group consisting of D-fructose, D-tagatose, maltulose, cellobiulose, and lactulose; wherein said cellobiose 2-epimerase catalyzes the following isomerizations:
  (a) 2-Epimerization
    epimerizing the 2-hydroxyl group of D-glucose and D-galactose to convert D-glucose and D-galactose into corresponding D-mannose and D-talose, and vice versa;
    epimerizing the 2-hydroxyl group of the reducing end glucose in maltose, cellobiose, and lactose to convert maltose, cellobiose, and lactose into corresponding epimaltose, epicellobiose, and epilactose; and
    epimerizing the 2-hydroxyl group of the reducing end glucose in a maltooligosaccharide and cellooligosaccharide, which have a glucose polymerization degree of 3 or higher, to convert the maltooligosaccharide and cellooligosaccharide into corresponding epimaltooligosaccharide and epicellooligosaccharide; and
  (b) Aldose-Ketose conversion
    converting D-glucose or D-mannose into D-fructose, and vice versa;
    converting D-galactose or D-talose into D-tagatose, and vice versa;
    converting maltose or epimaltose into maltulose;
    converting cellobiose or epicellobiose into cellobiulose; and
    converting lactose or epilactose into lactulose; and
  (2) decolorizing, deionizing, and concentrating the isomerized saccharide formed in step (1),
  wherein said cellobiose 2-epimerase is selected from the group consisting of a cellobiose 2-epimerase having the amino acid sequence of SEQ ID NO:10, and a recombinant cellobiose 2-epimerase having a variant amino acid sequence of SEQ ID NO:10, where one or more but less than 10 amino acid residues in SEQ ID NO:10 are replaced, deleted, or added without altering the enzyme activities in (a) and (b).

* * * * *